United States Patent
Fang et al.

(10) Patent No.: US 10,456,466 B2
(45) Date of Patent: Oct. 29, 2019

(54) ANTI-VEGF ANTIBODY

(71) Applicant: ZHUHAI ESSEX BIO-PHARMACEUTICAL CO., LTD., Zhuhai, Guangdong (CN)

(72) Inventors: Haizhou Fang, Guangdong (CN); Wei Qu, Guangdong (CN); Zanshun Zheng, Guangdong (CN); Lanfang Zhuang, Guangdong (CN); Xinzhi Wang, Guangdong (CN)

(73) Assignee: Zhuhai Essex Bio-Pharmaceutical Co., Ltd., Zhuhai (CN)

( * ) Notice: Subject to any disclaimer, the term of this patent is extended or adjusted under 35 U.S.C. 154(b) by 293 days.

(21) Appl. No.: 15/101,472

(22) PCT Filed: Jan. 6, 2015

(86) PCT No.: PCT/CN2015/070209
§ 371 (c)(1),
(2) Date: Jun. 3, 2016

(87) PCT Pub. No.: WO2016/109943
PCT Pub. Date: Jul. 14, 2016

(65) Prior Publication Data
US 2018/0169228 A1     Jun. 21, 2018

(51) Int. Cl.
*A61K 39/395* (2006.01)
*C07K 16/22* (2006.01)
*C12N 5/10* (2006.01)
*C12N 15/63* (2006.01)

(52) U.S. Cl.
CPC ........ *A61K 39/3955* (2013.01); *A61K 39/395* (2013.01); *C07K 16/22* (2013.01); *C07K 2317/22* (2013.01); *C07K 2317/24* (2013.01); *C07K 2317/565* (2013.01); *C07K 2317/622* (2013.01); *C07K 2317/76* (2013.01); *C12N 5/10* (2013.01); *C12N 15/63* (2013.01)

(58) Field of Classification Search
None
See application file for complete search history.

(56) References Cited

U.S. PATENT DOCUMENTS

| 6,342,221 B1 * | 1/2002 | Thorpe .............. A61K 39/3955 424/1.49 |
| 7,371,849 B2 | 5/2008 | Honda et al. |
| 2010/0120681 A1 | 5/2010 | Merchiers et al. |

FOREIGN PATENT DOCUMENTS

| CN | 101663319 A | 3/2010 |
| EP | 2471814 A1 | 7/2012 |
| WO | WO 2012/028716 A1 | 3/2012 |

OTHER PUBLICATIONS

Farajpour et al. (J. Biomol. Screening. 19(4): 547-555, 2014 (first published Dec. 2, 2013)).*

(Continued)

*Primary Examiner* — Christine J Saoud
(74) *Attorney, Agent, or Firm* — Myers Bigel, P.A.

(57) ABSTRACT

The present invention relates to antibodies which specifically bind vascular endothelial growth factor (VEGF), in particular heavy-chain antibodies, and more particularly single-domain antibodies. The present invention also relates to a method of producing the antibodies and the therapeutic uses thereof.

18 Claims, 11 Drawing Sheets
Specification includes a Sequence Listing.

(56) References Cited

OTHER PUBLICATIONS

Bell et al. "Differential tumor-targeting abilities of three single-domain antibody formats", *Cancer Letters* 289:81-90 (2010).
The CATT Research Group "Ranibizumab and Bevacizumab for Neovascular Age-Related Macular Degeneration", *N. Engl. J. Med.* 364(20):1897-1908 (2011).
Ferrara et al. "The biology of VEGF and its receptors", *Nature Medicine* 9(6):669-676 (2003).
Gengrinovitch et al. "Platelet Factor-4 Inhibits the Mitogenic Activity of $VEGF_{121}$ and $VEGF_{165}$ Using Several Concurrent Mechanisms", *The Journal of Biological Chemistry* 270(25):15059-15065 (1995).
Huang et al. "Vascular Endothelial Growth Factor—Fundamental Research and Experimental Study in Plastic Surgery", *Chinese J Reparative and Reconstructive Surgery* 16(1):64-69 (2002).
Keyt et al. "The Carboxyl-terminal Domain (111-165) of Vascular Endothelial Growth Factor is Critical for its Mitogenic Potency", *The Journal of Biological Chemistry* 271(13):7788-7795 (1996).
Klettner et al. "Treating Age-Related Macular Degeneration—Interaction of VEGF-Antagonists with their Target", *Mini-Reviews in Medicinal Chemistry* 9:1127-1135 (2009).
Li et al. "Bevacizumab for Neovascualr Age-Related Macular Degeneration in China", *Ophthalmology* 119(10):2087-2093 (2012).
Muyldermans "Single domain camel antibodies: current status", *Reviews in Molecular Biotechnology* 74:277-302 (2001).
Park et al. "The Vascular Endothelial Growth Factor (VEGF) Isoforms: Differential Deposition into the Subepithelial Extracellular Matrix and Bioactivity of Extracellular Matrix-bound VEGF", *Molecular Biology of the Cell* 4:1317-1326 (1993).
Saerens et al. "Single-domain antibodies as building blocks for novel therapeutics", *Current Opinion in Pharmacology* 8:600-608 (2008).
Stanfield et al. "Crystal Structure of a Shark Single-Domain Antibody V Region in Complex with Lysozyme", *Science* 305:1770-1773 (2004).
Van Bergen et al. "The role of different VEGF isoforms in scar formation after glaucoma filtration surgery", *Experimental Eye Research* 93:689-699 (2011).
Lien et al. "Therapeutic Anti-VEGF Antibodies", *Handbook of Experimental Pharmacology* 181(3):131-150 (2008).
Extended European Search Report corresponding to European Application No. 15864295.9 dated Sep. 12, 2017.

\* cited by examiner

Fig. 1. Detection of the purified hVEGF165
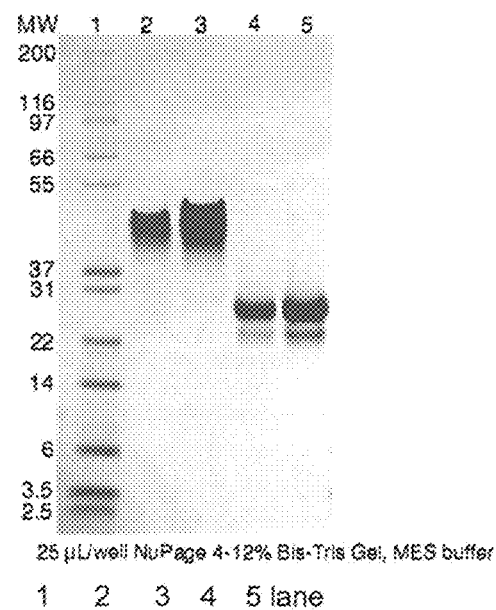
Fig. 2. Immunological assay
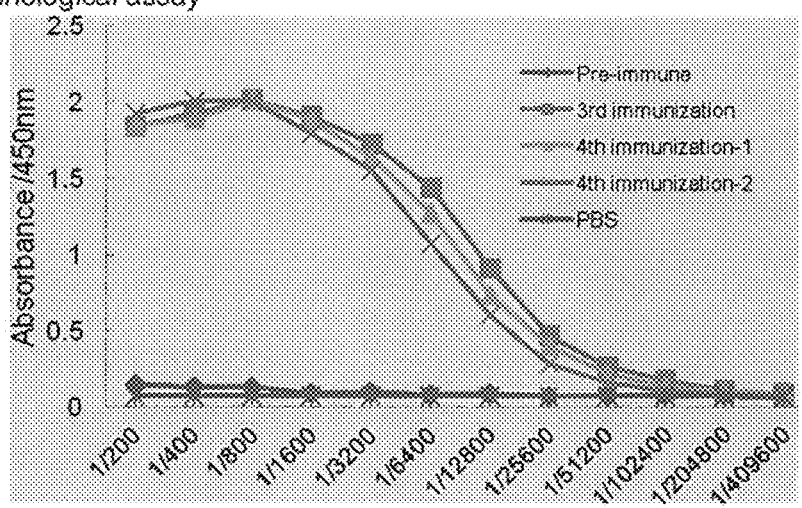

Fig. 3. Extraction and detection of total RNA from the lymphocyte
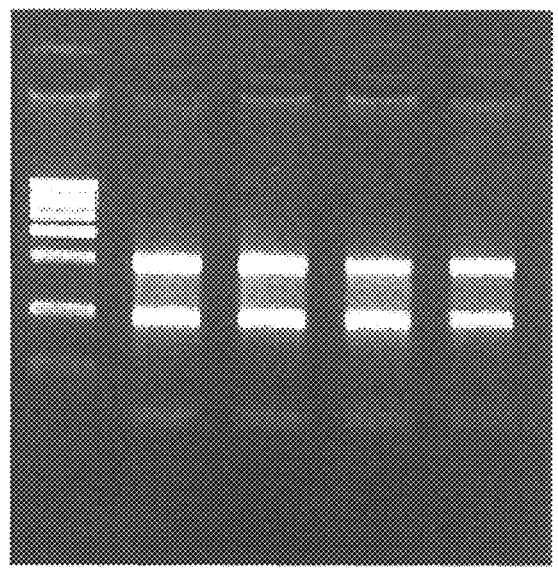
M : Marker DNA KB ladder ;
Lane 1-2 : cells from the 4th immunization
Lane 3-4 : cells from the 3rd immunization
Fig. 4. Amplification and purification of the $V_HH$ fragment
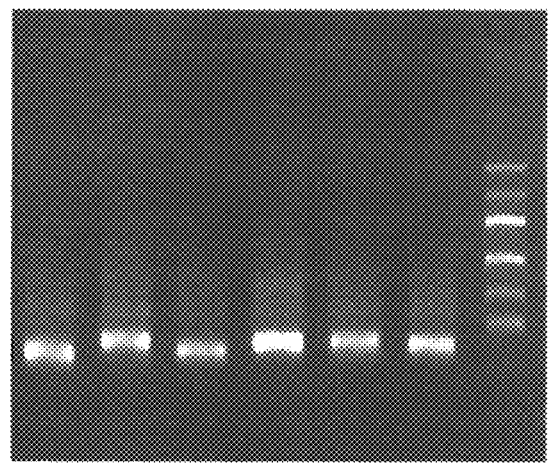
M : Marker DNA KB ladder ;
Lane 1-2 : cells from the 4th immunization
Lane 3-4 : cells from the 3rd immunization Fig. 5. Phagemid vector map
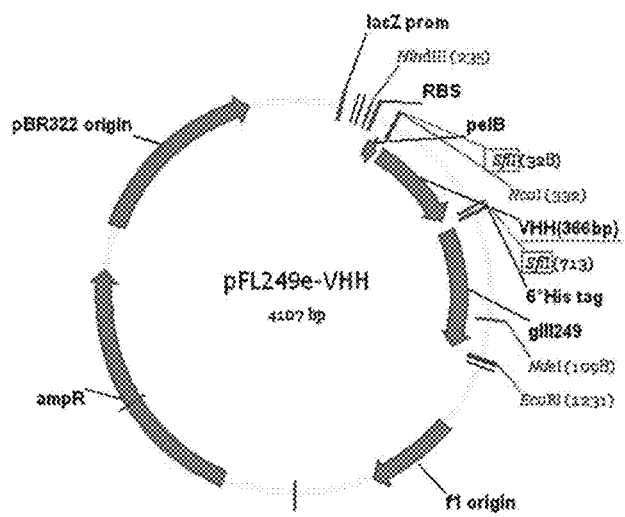
Fig. 6. Determination of the fragment insertion rate of the phage display library
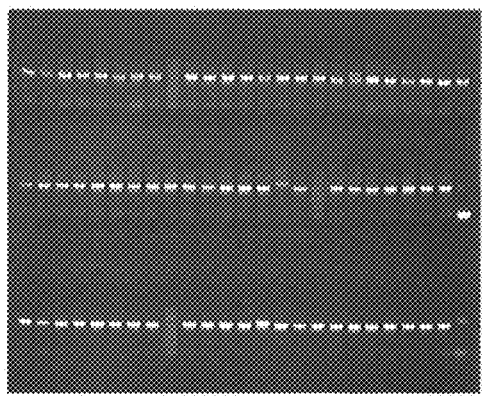

Fig. 7. The sequence diversity determination of the single-domain antibody library
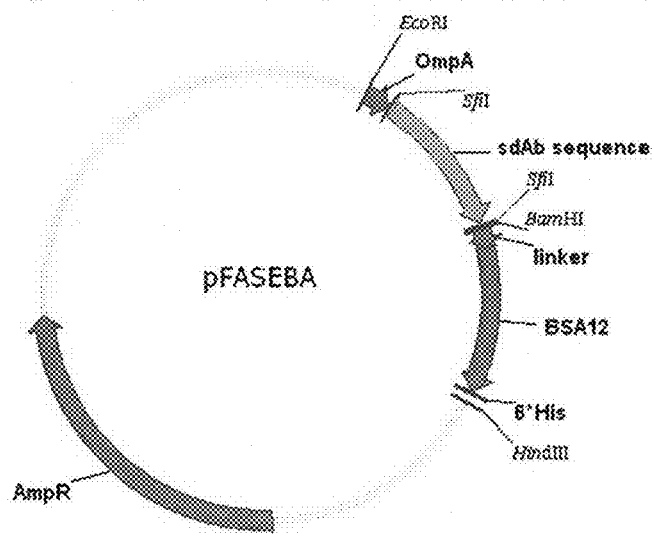
Fig. 8. Map of the vector specialized for FASEBA screening FASEBA Fig. 9. Affinity ranking
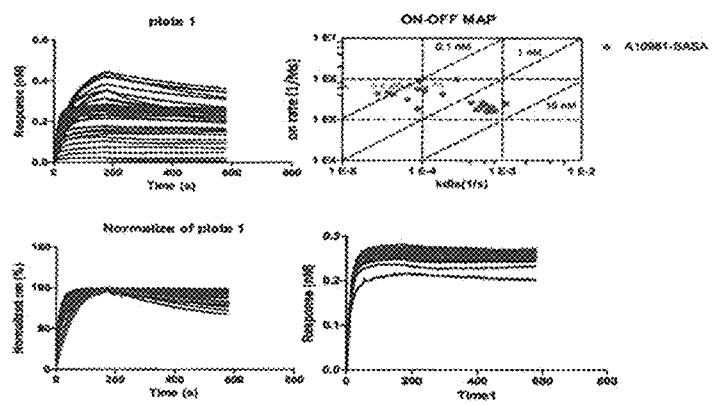
9A
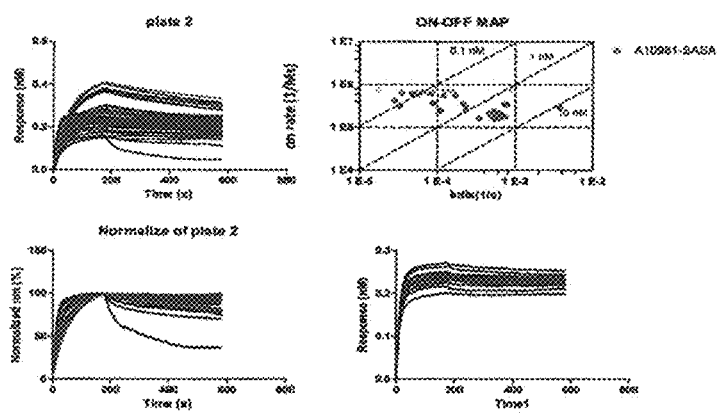
9B
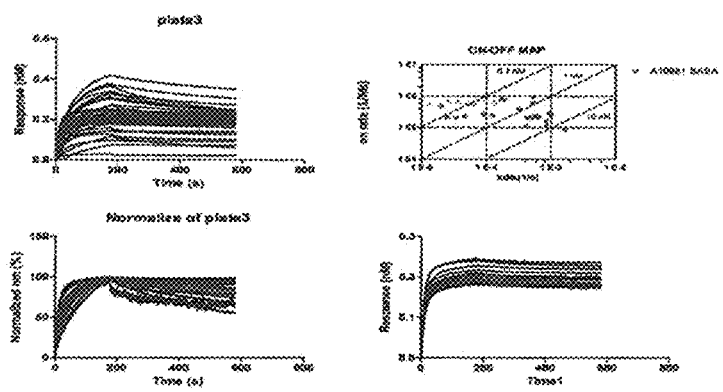
9C Fig. 10. The receptor competitive screening
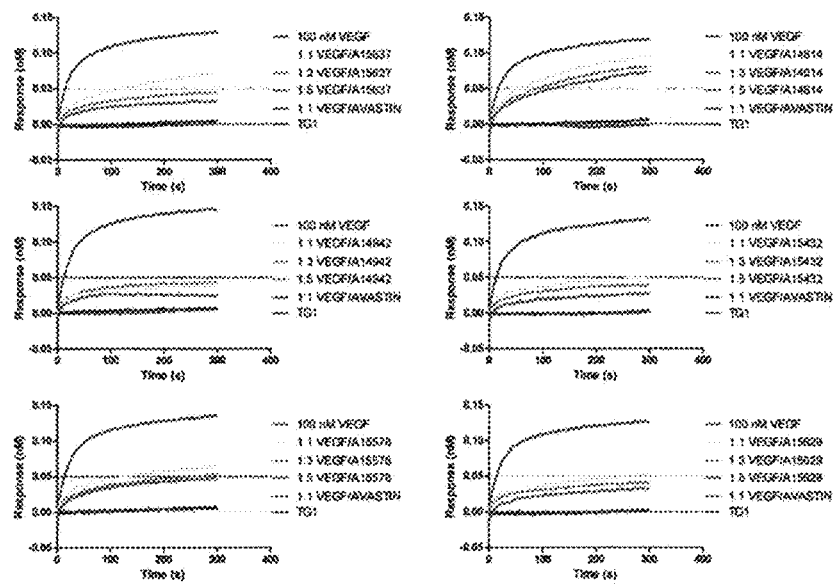
10A
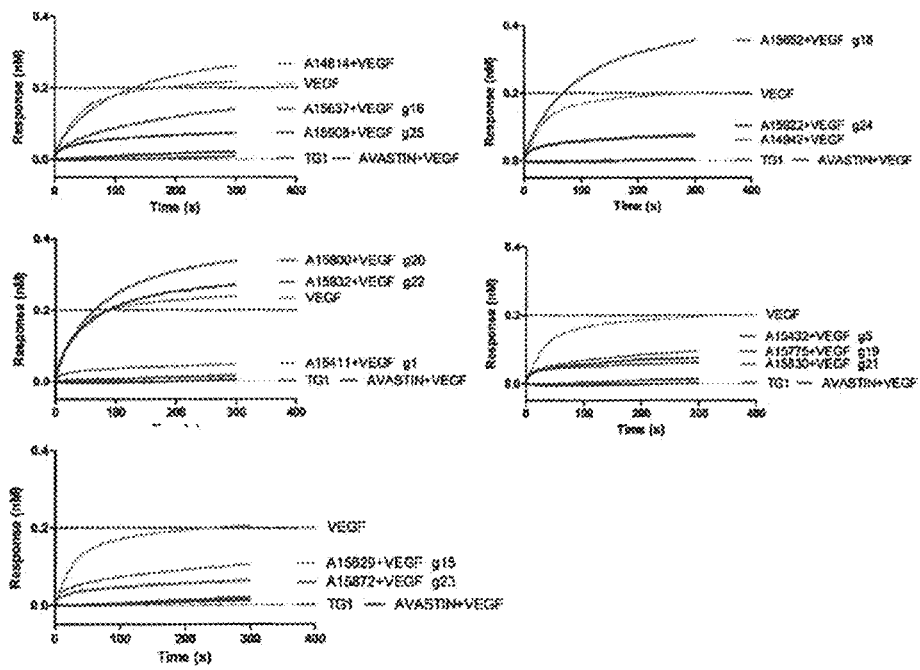
10B

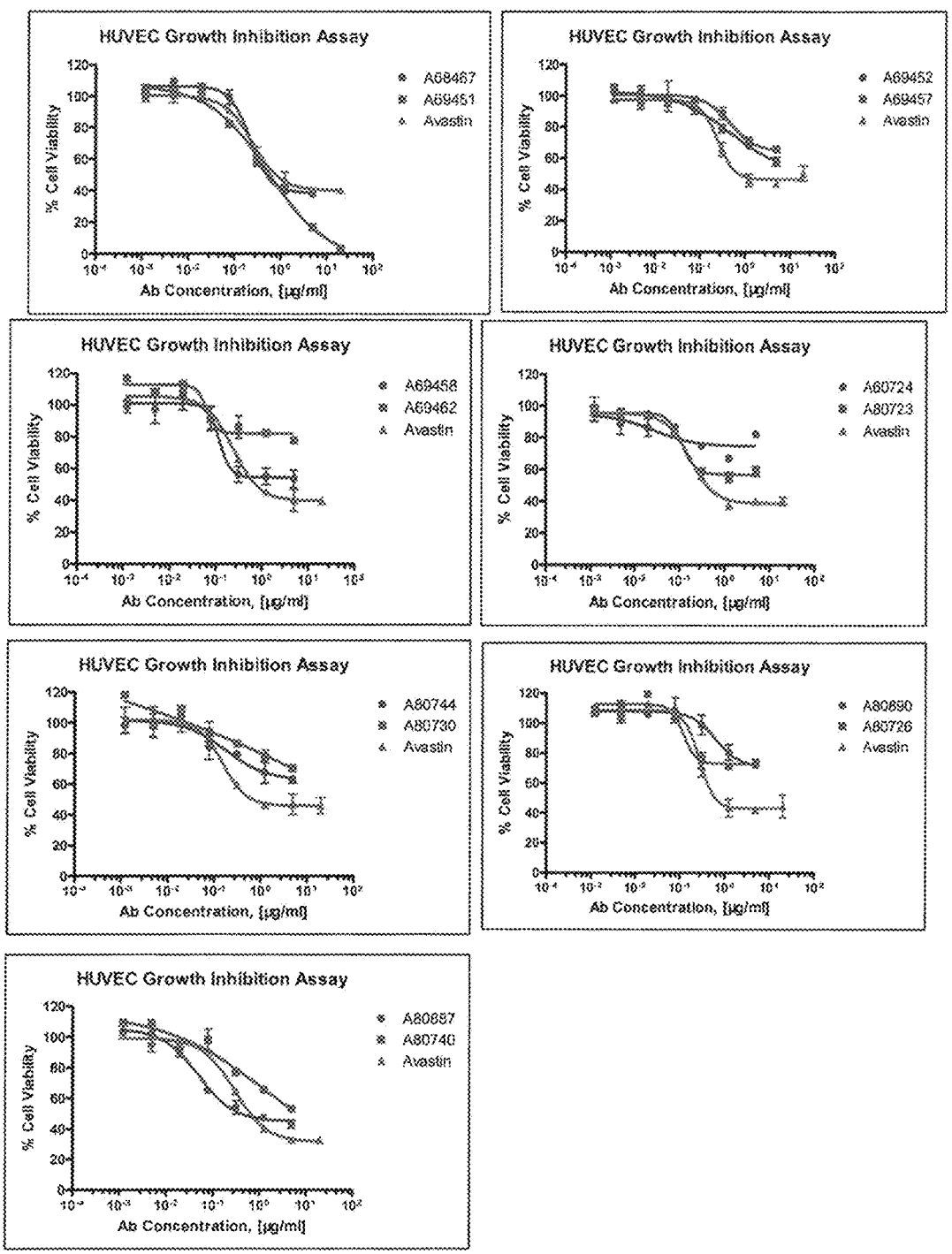
Fig. 11. HUVEC growth inhibition assay by the heavy chain antibody

Fig. 12

| | <FR1-Kabat> | <CDR1-Kabat><br><FR4-Kabat> | <FR2-Kabat> | <CDR2-Kabat> |
|---|---|---|---|---|
| | <FR3-Kabat> | <CDR3-Kabat> | | |
| A69451 | QVKLEESGGGLVQAGGSLRLSCAASGRTFS<br>RFTISRDNAKNTVYLQMNSLTPEDSAVYCAA | SYRLG<br>RGYSRSWNP-WSEYDY | WFRQAPGKEREFVA<br>WGQGTRVTVSS | AIS-WKDDTTYYADS---VKG |
| A69452 | GVQLVESGGGWVQAGDSLRLSCTASGSIPY<br>RFTISRDNAKNTVYLQMTSLKPEDTAVYYCNA | VPDMH<br>DVWSS---VA-LKLVEY | WYRQAPGQQRQLVA<br>WGQGIQVTVSS | TIT--RGGNTMYADS---VKG |
| A69457 | QVKLEESGGGLVQAGGSLRLSCAASGSIPY<br>RFTISRDNAKNTVYLQMTSLKPEDTAVYYCNA | VPDMH<br>DVWSS---VA-LKLVEY | WYRQAPGQQRQLVA<br>WGQGIQVTVSS | TIT--RGGNTMYADS---VKG |
| A69458 | DVQLVDSGGGLVQPGGSLTLSCVLSGRPFS<br>RFTVSRDNAKSAVNLQMNSLKREDTAVYYCAA | YYAVS<br>DTNVYASAT-LSNYAY | WFRQAPGGEREFVA<br>WGQGTQVTVSS | GIS-RSGGSVNFAGF---VKG |
| A69462 | QVQLVESGGGLVQAGGSLRLSCTDSGRTFG<br>RFTISRDNAKNTVCLQMNNLSPEDTAVYYCAA | AYNMG<br>NRGGN-YEK-VYLYNN | WFRQAPGKEREFVA<br>WGQGTQVTVSS | AIN-WSGISTYYTDS---VKG |
| A60724 | QVQLVESGGGLVQAGGSLRLSCTASGRTFG<br>RFTISRDNAKNTVYLQMNNLSPEDTAVYYCAA | AYNMG<br>NRGGN-YEK-VYLYNN | WFRQTPGKEREFVA<br>WGQGTQVTVSS | AIN-WSGISTYYTDS---VKG |
| A80723 | DVQLVESGGGLVQAGDSLRLSCAYSGATFS<br>RFFVSRDNDKSTMYLQMINLKPDDTAVYFCAA | NNVMG<br>GRRWR-ANR-ETHYDY | WFRQAPGRARDFVA<br>WGQGTQVTVSS | AFNGWSS-VTEYADS---VKG |
| A80744 | AVQLVESGGGLVQAGGSLRLSCAASGLNFR<br>RATISRDNAENTVYLQMNSLKPEDTAVYYCAA | TYTIG<br>GRNTGGYTRLWRSYDY | WFRQAPGKEREFIV<br>WGQGTQVTVSS | GIT-WGGIIDSIDS---MKG |
| A80730 | QVQLVESGGGLVQAGGSLRLSCAASGRAPE<br>RFTISRNNAKNTVYLQMNSLKPEDTAVYYCAA | TYAMG<br>DRSAR-WEP---GTHY | WFRQAPGKEREFVA<br>WGQGTQVTVSS | HII-VTGDRTYYADS---VKG |
| A80890 | QVKLEESGGGLVQAGGSLRLSCAASGSISH | VPNMH | WYRQAPGQKRQLVA | TIT--RGGNTMYADS---VKG |

Fig. 12 Cont'd

RFTISRENAKNTIYLQMTTLKPEDTAVYYCNA DVWSS-AL--FKYVEY WGQGTQVTVSS

A80726 QVKLEESGGGLVQAGDSLRLSCTASGGTYS SGVMG WFRQAPGKERDFVA SIN-WSG-VTDYSDS-----VKG
RFFISRDTAKSTVYLHMFSLKADDTAVYFCAA GSRWR-ANS-GRHYDY WGQGTQVTVSS

A80887 QVKLEESGGGLVQTGGSLRLSCAASGRTFS SYAMG WFRQAPGKEREFVA AIS-WSGGHTYYADSAVDSVRG
RFTISRGNAKNTVYLQMNNLKPEDTAVYYCAA DFGTRLRFT-TNDYQY WGQGTQVTVSS

A80740 EVQLVDSGGGLVQAGGSLRLSCAASGSISY VPDMH WYRQAPGQQRQLVA TIT-RGGNTMYADS-----VKG
RFTISRDNAKNTVYLQMTSLKPEDTAVYYCNA DVWSS---VL-FKLVEY WGQGTQVTVSS

Fig. 13. A schematic representation of the subintestinal vessels of the zebra fish
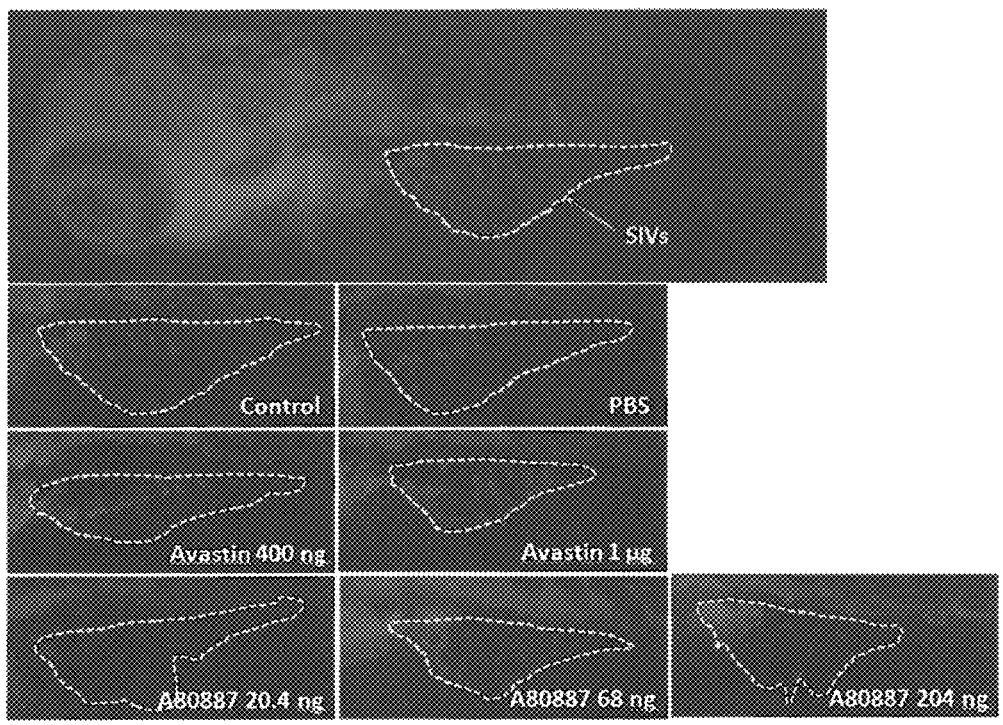
Fig. 14. The area of the subintestinal vessels
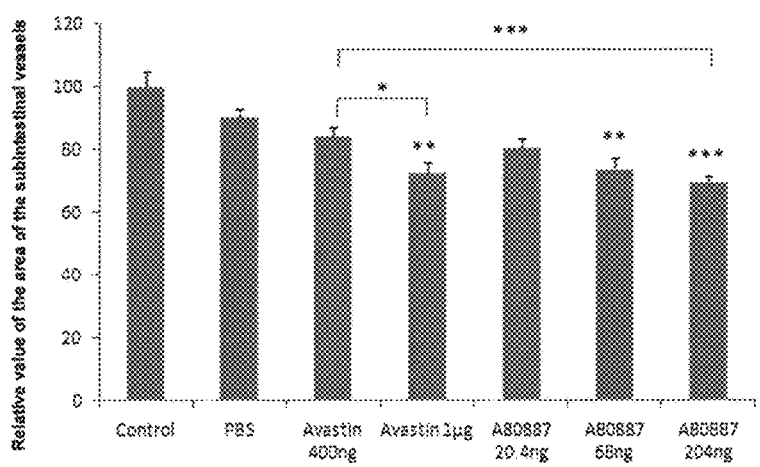
The data are shown as mean ± SE, n=15, *$p < 0.05$, $p < 0.01$, *$p < 0.001$, compared with PBS.

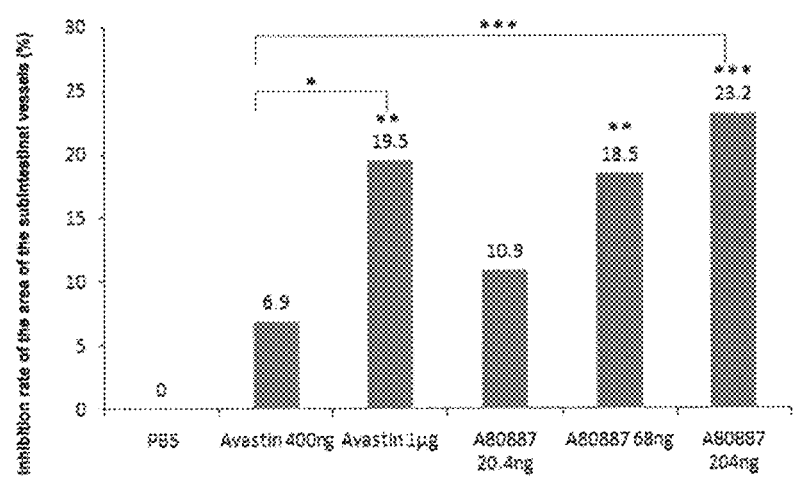
Fig. 15. The inhibition rate of the area of the subintestinal vessels
The data are shown as mean ± SE, n=15, *p < 0.05, p < 0.01, *p < 0.001, compared with PBS.

SEQUENCE LISTING

<160> NUMBER OF SEQ ID NOS: 71

<210> SEQ ID NO 1
<211> LENGTH: 5
<212> TYPE: PRT
<213> ORGANISM: Lama pacos

<400> SEQUENCE: 1

Ser Tyr Ala Met Gly
1               5

<210> SEQ ID NO 2
<211> LENGTH: 21
<212> TYPE: PRT
<213> ORGANISM: Lama pacos

<400> SEQUENCE: 2

Ala Ile Ser Trp Ser Gly Gly His Thr Tyr Tyr Ala Asp Ser Ala Val
1               5                   10                  15

Asp Ser Val Arg Gly
            20

<210> SEQ ID NO 3
<211> LENGTH: 15
<212> TYPE: PRT
<213> ORGANISM: Lama pacos

<400> SEQUENCE: 3

Asp Phe Gly Thr Arg Leu Arg Phe Thr Thr Asn Asp Tyr Gln Tyr
1               5                   10                  15

<210> SEQ ID NO 4
<211> LENGTH: 5
<212> TYPE: PRT
<213> ORGANISM: Lama pacos

<400> SEQUENCE: 4

Asn Asn Val Met Gly
1               5

<210> SEQ ID NO 5
<211> LENGTH: 17
<212> TYPE: PRT
<213> ORGANISM: Lama pacos

<400> SEQUENCE: 5

Ala Phe Asn Gly Trp Ser Ser Val Thr Glu Tyr Ala Asp Ser Val Lys
1               5                   10                  15

Gly

<210> SEQ ID NO 6
<211> LENGTH: 14
<212> TYPE: PRT
<213> ORGANISM: Lama pacos

<400> SEQUENCE: 6

Gly Arg Arg Trp Arg Ala Asn Arg Glu Thr His Tyr Asp Tyr
1               5                   10

<210> SEQ ID NO 7
<211> LENGTH: 5
<212> TYPE: PRT
<213> ORGANISM: Lama pacos

<400> SEQUENCE: 7

Tyr Tyr Ala Val Ser
1               5

<210> SEQ ID NO 8
<211> LENGTH: 17
<212> TYPE: PRT
<213> ORGANISM: Lama pacos

<400> SEQUENCE: 8

Gly Ile Ser Arg Ser Gly Gly Ser Val Asn Phe Ala Gly Phe Val Lys
1               5                   10                  15

Gly

<210> SEQ ID NO 9
<211> LENGTH: 15
<212> TYPE: PRT
<213> ORGANISM: Lama pacos

<400> SEQUENCE: 9

Asp Thr Asn Val Tyr Ala Ser Ala Thr Leu Ser Asn Tyr Ala Tyr
1               5                   10                  15

<210> SEQ ID NO 10
<211> LENGTH: 5
<212> TYPE: PRT
<213> ORGANISM: Lama pacos

<400> SEQUENCE: 10

Ser Tyr Arg Leu Gly
1               5

<210> SEQ ID NO 11
<211> LENGTH: 17
<212> TYPE: PRT
<213> ORGANISM: Lama pacos

<400> SEQUENCE: 11

Ala Ile Ser Trp Lys Asp Asp Thr Thr Tyr Tyr Ala Asp Ser Val Lys
1               5                   10                  15

Gly

<210> SEQ ID NO 12
<211> LENGTH: 15
<212> TYPE: PRT
<213> ORGANISM: Lama pacos

<400> SEQUENCE: 12

Arg Gly Tyr Ser Arg Ser Trp Asn Pro Trp Ser Glu Tyr Asp Tyr
1               5                   10                  15

<210> SEQ ID NO 13
<211> LENGTH: 5
<212> TYPE: PRT
<213> ORGANISM: Lama pacos

<400> SEQUENCE: 13

Val Pro Asp Met His
1               5

<210> SEQ ID NO 14
<211> LENGTH: 16
<212> TYPE: PRT

<213> ORGANISM: Lama pacos

<400> SEQUENCE: 14

Thr Ile Thr Arg Gly Gly Asn Thr Met Tyr Ala Asp Ser Val Lys Gly
1               5                   10                  15

<210> SEQ ID NO 15
<211> LENGTH: 13
<212> TYPE: PRT
<213> ORGANISM: Lama pacos

<400> SEQUENCE: 15

Asp Val Trp Ser Ser Val Ala Leu Lys Leu Val Glu Tyr
1               5                   10

<210> SEQ ID NO 16
<211> LENGTH: 5
<212> TYPE: PRT
<213> ORGANISM: Lama pacos

<400> SEQUENCE: 16

Ala Tyr Asn Met Gly
1               5

<210> SEQ ID NO 17
<211> LENGTH: 17
<212> TYPE: PRT
<213> ORGANISM: Lama pacos

<400> SEQUENCE: 17

Ala Ile Asn Trp Ser Gly Ile Ser Thr Tyr Tyr Thr Asp Ser Val Lys
1               5                   10                  15

Gly

<210> SEQ ID NO 18
<211> LENGTH: 14
<212> TYPE: PRT
<213> ORGANISM: Lama pacos

<400> SEQUENCE: 18

Asn Arg Gly Gly Asn Tyr Glu Lys Val Tyr Leu Tyr Asn Asn
1               5                   10

<210> SEQ ID NO 19
<211> LENGTH: 5
<212> TYPE: PRT
<213> ORGANISM: Lama pacos

<400> SEQUENCE: 19

Thr Tyr Thr Ile Gly
1               5

<210> SEQ ID NO 20
<211> LENGTH: 17
<212> TYPE: PRT
<213> ORGANISM: Lama pacos

<400> SEQUENCE: 20

Gly Ile Thr Trp Gly Gly Gly Ile Ile Asp Ser Ile Asp Ser Met Lys
1               5                   10                  15

Gly

<210> SEQ ID NO 21

<210> SEQ ID NO 21
<211> LENGTH: 16
<212> TYPE: PRT
<213> ORGANISM: Lama pacos

<400> SEQUENCE: 21

Gly Arg Asn Thr Gly Gly Tyr Thr Arg Leu Trp Arg Ser Tyr Asp Tyr
1               5                   10                  15

<210> SEQ ID NO 22
<211> LENGTH: 5
<212> TYPE: PRT
<213> ORGANISM: Lama pacos

<400> SEQUENCE: 22

Thr Tyr Ala Met Gly
1               5

<210> SEQ ID NO 23
<211> LENGTH: 17
<212> TYPE: PRT
<213> ORGANISM: Lama pacos

<400> SEQUENCE: 23

His Ile Ile Val Thr Gly Asp Arg Thr Tyr Tyr Ala Asp Ser Val Lys
1               5                   10                  15

Gly

<210> SEQ ID NO 24
<211> LENGTH: 12
<212> TYPE: PRT
<213> ORGANISM: Lama pacos

<400> SEQUENCE: 24

Asp Arg Ser Ala Arg Trp Glu Pro Gly Thr His Tyr
1               5                   10

<210> SEQ ID NO 25
<211> LENGTH: 5
<212> TYPE: PRT
<213> ORGANISM: Lama pacos

<400> SEQUENCE: 25

Val Pro Asn Met His
1               5

<210> SEQ ID NO 26
<211> LENGTH: 16
<212> TYPE: PRT
<213> ORGANISM: Lama pacos

<400> SEQUENCE: 26

Thr Ile Thr Arg Gly Gly Asn Thr Met Tyr Ala Asp Ser Val Lys Gly
1               5                   10                  15

<210> SEQ ID NO 27
<211> LENGTH: 13
<212> TYPE: PRT
<213> ORGANISM: Lama pacos

<400> SEQUENCE: 27

Asp Val Trp Ser Ser Ala Leu Phe Lys Tyr Val Glu Tyr
1               5                   10

<210> SEQ ID NO 28

```
<211> LENGTH: 5
<212> TYPE: PRT
<213> ORGANISM: Lama pacos

<400> SEQUENCE: 28

Ser Gly Val Met Gly
1               5

<210> SEQ ID NO 29
<211> LENGTH: 16
<212> TYPE: PRT
<213> ORGANISM: Lama pacos

<400> SEQUENCE: 29

Ser Ile Asn Trp Ser Gly Val Thr Asp Tyr Ser Asp Ser Val Lys Gly
1               5                   10                  15

<210> SEQ ID NO 30
<211> LENGTH: 14
<212> TYPE: PRT
<213> ORGANISM: Lama pacos

<400> SEQUENCE: 30

Gly Ser Arg Trp Arg Ala Asn Ser Gly Arg His Tyr Asp Tyr
1               5                   10

<210> SEQ ID NO 31
<211> LENGTH: 5
<212> TYPE: PRT
<213> ORGANISM: Lama pacos

<400> SEQUENCE: 31

Val Pro Asp Met His
1               5

<210> SEQ ID NO 32
<211> LENGTH: 16
<212> TYPE: PRT
<213> ORGANISM: Lama pacos

<400> SEQUENCE: 32

Thr Ile Thr Arg Gly Gly Asn Thr Met Tyr Ala Asp Ser Val Lys Gly
1               5                   10                  15

<210> SEQ ID NO 33
<211> LENGTH: 13
<212> TYPE: PRT
<213> ORGANISM: Lama pacos

<400> SEQUENCE: 33

Asp Val Trp Ser Ser Val Leu Phe Lys Leu Val Glu Tyr
1               5                   10

<210> SEQ ID NO 34
<211> LENGTH: 128
<212> TYPE: PRT
<213> ORGANISM: Artificial Sequence
<220> FEATURE:
<223> OTHER INFORMATION: Variable Region Sequence

<400> SEQUENCE: 34

Gln Val Lys Leu Glu Glu Ser Gly Gly Gly Leu Val Gln Thr Gly Gly
1               5                   10                  15

Ser Leu Arg Leu Ser Cys Ala Ala Ser Gly Arg Thr Phe Ser Ser Tyr
                20                  25                  30
```

Ala Met Gly Trp Phe Arg Gln Ala Pro Gly Lys Glu Arg Glu Phe Val
        35                  40                  45

Ala Ala Ile Ser Trp Ser Gly Gly His Thr Tyr Tyr Ala Asp Ser Ala
    50                  55                  60

Val Asp Ser Val Arg Gly Arg Phe Thr Ile Ser Arg Gly Asn Ala Lys
65                  70                  75                  80

Asn Thr Val Tyr Leu Gln Met Asn Asn Leu Lys Pro Glu Asp Thr Ala
                85                  90                  95

Val Tyr Tyr Cys Ala Ala Asp Phe Gly Thr Arg Leu Arg Phe Thr Thr
            100                 105                 110

Asn Asp Tyr Gln Tyr Trp Gly Gln Gly Thr Gln Val Thr Val Ser Ser
        115                 120                 125

<210> SEQ ID NO 35
<211> LENGTH: 123
<212> TYPE: PRT
<213> ORGANISM: Artificial
<220> FEATURE:
<223> OTHER INFORMATION: Variable Region Sequence

<400> SEQUENCE: 35

Asp Val Gln Leu Val Glu Ser Gly Gly Gly Leu Val Gln Ala Gly Asp
1               5                   10                  15

Ser Leu Arg Leu Ser Cys Ala Tyr Ser Gly Ala Thr Phe Ser Asn Asn
            20                  25                  30

Val Met Gly Trp Phe Arg Gln Ala Pro Gly Arg Ala Arg Asp Phe Val
        35                  40                  45

Ala Ala Phe Asn Gly Trp Ser Ser Val Thr Glu Tyr Ala Asp Ser Val
    50                  55                  60

Lys Gly Arg Phe Phe Val Ser Arg Asp Asn Asp Lys Ser Thr Met Tyr
65                  70                  75                  80

Leu Gln Met Ile Asn Leu Lys Pro Asp Asp Thr Ala Val Tyr Phe Cys
                85                  90                  95

Ala Ala Gly Arg Arg Trp Arg Ala Asn Arg Glu Thr His Tyr Asp Tyr
            100                 105                 110

Trp Gly Gln Gly Thr Gln Val Thr Val Ser Ser
        115                 120

<210> SEQ ID NO 36
<211> LENGTH: 124
<212> TYPE: PRT
<213> ORGANISM: Artificial
<220> FEATURE:
<223> OTHER INFORMATION: Variable Region Sequence

<400> SEQUENCE: 36

Asp Val Gln Leu Val Asp Ser Gly Gly Gly Leu Val Gln Pro Gly Gly
1               5                   10                  15

Ser Leu Thr Leu Ser Cys Val Leu Ser Gly Arg Pro Phe Ser Tyr Tyr
            20                  25                  30

Ala Val Ser Trp Phe Arg Gln Ala Pro Gly Gly Glu Arg Glu Phe Val
        35                  40                  45

Ala Gly Ile Ser Arg Ser Gly Ser Val Asn Phe Ala Gly Phe Val
    50                  55                  60

Lys Gly Arg Phe Thr Val Ser Arg Asp Asn Ala Lys Ser Ala Val Asn
65                  70                  75                  80

Leu Gln Met Asn Ser Leu Lys Arg Glu Asp Thr Ala Val Tyr Tyr Cys

```
                    85                  90                  95

Ala Ala Asp Thr Asn Val Tyr Ala Ser Ala Thr Leu Ser Asn Tyr Ala
                100                 105                 110

Tyr Trp Gly Gln Gly Thr Gln Val Thr Val Ser Ser
        115                 120

<210> SEQ ID NO 37
<211> LENGTH: 124
<212> TYPE: PRT
<213> ORGANISM: Artificial
<220> FEATURE:
<223> OTHER INFORMATION: Variable Region Sequence

<400> SEQUENCE: 37

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
                20                  25                  30

Arg Leu Gly Trp Phe Arg Gln Ala Pro Gly Lys Glu Arg Glu Phe Val
            35                  40                  45

Ala Ala Ile Ser Trp Lys Asp Asp Thr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Thr Pro Glu Asp Ser Ala Val Tyr Ser Cys
                85                  90                  95

Ala Ala Arg Gly Tyr Ser Arg Ser Trp Asn Pro Trp Ser Glu Tyr Asp
                100                 105                 110

Tyr Trp Gly Gln Gly Thr Arg Val Thr Val Ser Ser
        115                 120

<210> SEQ ID NO 38
<211> LENGTH: 121
<212> TYPE: PRT
<213> ORGANISM: Artificial
<220> FEATURE:
<223> OTHER INFORMATION: Variable Region Sequence

<400> SEQUENCE: 38

Gly Val Gln Leu Val Glu Ser Gly Gly Gly Trp Val Gln Ala Gly Asp
1               5                   10                  15

Ser Leu Arg Leu Ser Cys Thr Ala Ser Gly Ser Ile Pro Tyr Val Pro
                20                  25                  30

Asp Met His Trp Tyr Arg Gln Ala Pro Gly Gln Gln Arg Gln Leu Val
            35                  40                  45

Ala Thr Ile Thr Arg Gly Gly Asn Thr Met Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
                85                  90                  95

Ala Asp Val Trp Ser Ser Val Ala Leu Lys Leu Val Glu Tyr Trp Gly
                100                 105                 110

Gln Gly Ile Gln Val Thr Val Ser Ser
        115                 120

<210> SEQ ID NO 39
<211> LENGTH: 121
```

```
<212> TYPE: PRT
<213> ORGANISM: Artificial
<220> FEATURE:
<223> OTHER INFORMATION: Variable Region Sequence

<400> SEQUENCE: 39

Gln Val Lys Leu Glu Glu Ser Gly Gly Gly Leu Val Gln Ala Gly Gly
1               5                   10                  15

Ser Leu Arg Leu Ser Cys Ala Ala Ser Gly Ser Ile Pro Tyr Val Pro
            20                  25                  30

Asp Met His Trp Tyr Arg Gln Ala Pro Gly Gln Gln Arg Gln Leu Val
        35                  40                  45

Ala Thr Ile Thr Arg Gly Gly Asn Thr Met Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys Asn
                85                  90                  95

Ala Asp Val Trp Ser Ser Val Ala Leu Lys Leu Val Glu Tyr Trp Gly
            100                 105                 110

Gln Gly Ile Gln Val Thr Val Ser Ser
        115                 120

<210> SEQ ID NO 40
<211> LENGTH: 123
<212> TYPE: PRT
<213> ORGANISM: Artificial
<220> FEATURE:
<223> OTHER INFORMATION: Variable Region Sequence

<400> SEQUENCE: 40

Gln Val Gln Leu Val Glu Ser Gly Gly Gly Leu Val Gln Ala Gly Gly
1               5                   10                  15

Ser Leu Arg Leu Ser Cys Thr Asp Ser Gly Arg Thr Phe Gly Ala Tyr
            20                  25                  30

Asn Met Gly Trp Phe Arg Gln Ala Pro Gly Lys Glu Arg Glu Phe Val
        35                  40                  45

Ala Ala Ile Asn Trp Ser Gly Ile Ser Thr Tyr Tyr Thr Asp Ser Val
    50                  55                  60

Lys Gly Arg Phe Thr Ile Ser Arg Asp Asn Ala Lys Asn Thr Val Cys
65                  70                  75                  80

Leu Gln Met Asn Asn Leu Ser Pro Glu Asp Thr Ala Val Tyr Tyr Cys
                85                  90                  95

Ala Ala Asn Arg Gly Gly Asn Tyr Glu Lys Val Tyr Leu Tyr Asn Asn
            100                 105                 110

Trp Gly Gln Gly Thr Gln Val Thr Val Ser Ser
        115                 120

<210> SEQ ID NO 41
<211> LENGTH: 123
<212> TYPE: PRT
<213> ORGANISM: Artificial
<220> FEATURE:
<223> OTHER INFORMATION: Variable Region Sequence

<400> SEQUENCE: 41

Gln Val Gln Leu Val Glu Ser Gly Gly Gly Leu Val Gln Ala Gly Gly
1               5                   10                  15

Ser Leu Arg Leu Ser Cys Thr Ala Ser Gly Arg Thr Phe Gly Ala Tyr
```

```
                    20                  25                  30
Asn Met Gly Trp Phe Arg Gln Thr Pro Gly Lys Glu Arg Glu Phe Val
                35                  40                  45

Ala Ala Ile Asn Trp Ser Gly Ile Ser Thr Tyr Tyr Thr Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Asn Leu Ser Pro Glu Asp Thr Ala Val Tyr Tyr Cys
                85                  90                  95

Ala Ala Asn Arg Gly Gly Asn Tyr Glu Lys Val Tyr Leu Tyr Asn Asn
            100                 105                 110

Trp Gly Gln Gly Thr Gln Val Thr Val Ser Ser
            115                 120

<210> SEQ ID NO 42
<211> LENGTH: 125
<212> TYPE: PRT
<213> ORGANISM: Artificial
<220> FEATURE:
<223> OTHER INFORMATION: Variable Region Sequence

<400> SEQUENCE: 42

Ala Val Gln Leu Val Glu Ser Gly Gly Gly Leu Val Gln Ala Gly Gly
1               5                   10                  15

Ser Leu Arg Leu Ser Cys Ala Ala Ser Gly Leu Asn Phe Arg Thr Tyr
            20                  25                  30

Thr Ile Gly Trp Phe Arg Gln Ala Pro Gly Lys Glu Arg Glu Phe Ile
            35                  40                  45

Val Gly Ile Thr Trp Gly Gly Ile Ile Asp Ser Ile Asp Ser Met
            50                  55                  60

Lys Gly Arg Ala Thr Ile Ser Arg Asp Asn Ala Glu Asn Thr Val Tyr
65                  70                  75                  80

Leu Gln Met Asn Ser Leu Lys Pro Glu Asp Thr Ala Val Tyr Ser Cys
                85                  90                  95

Ala Ala Gly Arg Asn Thr Gly Tyr Thr Arg Leu Trp Arg Ser Tyr
            100                 105                 110

Asp Tyr Trp Gly Gln Gly Thr Gln Val Thr Val Ser Ser
            115                 120                 125

<210> SEQ ID NO 43
<211> LENGTH: 121
<212> TYPE: PRT
<213> ORGANISM: Artificial
<220> FEATURE:
<223> OTHER INFORMATION: Variable Region Sequence

<400> SEQUENCE: 43

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ala Pro Glu Thr Tyr
            20                  25                  30

Ala Met Gly Trp Phe Arg Gln Ala Pro Gly Lys Glu Arg Glu Phe Val
            35                  40                  45

Ala His Ile Ile Val Thr Gly Asp Arg Thr Tyr Tyr Ala Asp Ser Val
            50                  55                  60

Lys Gly Arg Phe Thr Ile Ser Arg Asn Asn Ala Lys Asn Thr Val Tyr
65                  70                  75                  80
```

Leu Gln Met Asn Ser Leu Lys Pro Glu Asp Thr Ala Val Tyr Tyr Cys
                85                  90                  95

Ala Ala Asp Arg Ser Ala Arg Trp Glu Pro Gly Thr His Tyr Trp Gly
            100                 105                 110

Gln Gly Thr Gln Val Thr Val Ser Ser
        115                 120

<210> SEQ ID NO 44
<211> LENGTH: 121
<212> TYPE: PRT
<213> ORGANISM: Artificial
<220> FEATURE:
<223> OTHER INFORMATION: Variable Region Sequence

<400> SEQUENCE: 44

Gln Val Lys Leu Glu Glu Ser Gly Gly Gly Leu Val Gln Ala Gly Gly
1               5                   10                  15

Ser Leu Arg Leu Ser Cys Ala Ala Ser Gly Ser Ile Ser His Val Pro
            20                  25                  30

Asn Met His Trp Tyr Arg Gln Ala Pro Gly Gln Lys Arg Gln Leu Val
        35                  40                  45

Ala Thr Ile Thr Arg Gly Gly Asn Thr Met Tyr Ala Asp Ser Val Lys
    50                  55                  60

Gly Arg Phe Thr Ile Ser Arg Glu Asn Ala Lys Asn Thr Ile Tyr Leu
65                  70                  75                  80

Gln Met Thr Thr Leu Lys Pro Glu Asp Thr Ala Val Tyr Tyr Cys Asn
                85                  90                  95

Ala Asp Val Trp Ser Ser Ala Leu Phe Lys Tyr Val Glu Tyr Trp Gly
            100                 105                 110

Gln Gly Thr Gln Val Thr Val Ser Ser
        115                 120

<210> SEQ ID NO 45
<211> LENGTH: 122
<212> TYPE: PRT
<213> ORGANISM: Artificial
<220> FEATURE:
<223> OTHER INFORMATION: Variable Region Sequence

<400> SEQUENCE: 45

Gln Val Lys Leu Glu Glu Ser Gly Gly Gly Leu Val Gln Ala Gly Asp
1               5                   10                  15

Ser Leu Arg Leu Ser Cys Thr Ala Ser Gly Gly Thr Tyr Ser Ser Gly
            20                  25                  30

Val Met Gly Trp Phe Arg Gln Ala Pro Gly Lys Glu Arg Asp Phe Val
        35                  40                  45

Ala Ser Ile Asn Trp Ser Gly Val Thr Asp Tyr Ser Asp Ser Val Lys
    50                  55                  60

Gly Arg Phe Phe Ile Ser Arg Asp Thr Ala Lys Ser Thr Val Tyr Leu
65                  70                  75                  80

His Met Phe Ser Leu Lys Ala Asp Asp Thr Ala Val Tyr Phe Cys Ala
                85                  90                  95

Ala Gly Ser Arg Trp Arg Ala Asn Ser Gly Arg His Tyr Asp Tyr Trp
            100                 105                 110

Gly Gln Gly Thr Gln Val Thr Val Ser Ser
        115                 120

<210> SEQ ID NO 46

<211> LENGTH: 121
<212> TYPE: PRT
<213> ORGANISM: Artificial
<220> FEATURE:
<223> OTHER INFORMATION: Variable Region Sequence

<400> SEQUENCE: 46

Glu Val Gln Leu Val Asp Ser Gly Gly Gly Leu Val Gln Ala Gly Gly
1               5                   10                  15
Ser Leu Arg Leu Ser Cys Ala Ala Ser Gly Ser Ile Ser Tyr Val Pro
            20                  25                  30
Asp Met His Trp Tyr Arg Gln Ala Pro Gly Gln Gln Arg Gln Leu Val
        35                  40                  45
Ala Thr Ile Thr Arg Gly Gly Asn Thr Met Tyr Ala Asp Ser Val Lys
    50                  55                  60
Gly Arg Phe Thr Ile Ser Arg Asp Asn Ala Lys Asn Thr Val Tyr Leu
65                  70                  75                  80
Gln Met Thr Ser Leu Lys Pro Glu Asp Thr Ala Val Tyr Tyr Cys Asn
                85                  90                  95
Ala Asp Val Trp Ser Ser Val Leu Phe Lys Leu Val Glu Tyr Trp Gly
            100                 105                 110
Gln Gly Thr Gln Val Thr Val Ser Ser
        115                 120

<210> SEQ ID NO 47
<211> LENGTH: 384
<212> TYPE: DNA
<213> ORGANISM: Artificial
<220> FEATURE:
<223> OTHER INFORMATION: Nucleotide Sequence of Variable Region

<400> SEQUENCE: 47
caggtaaagc tggaggagtc tgggggagga ttggtgcaga ctgggggctc tctgagactc       60
tcctgtgcag cctctggacg cacctttcagt tcctatgcca tggctggtt ccgccaggct     120
ccagggaagg agcgtgagtt tgtagcagct attagctgga gtggtggtca cacatactat    180
gcagactcag ctgttgactc cgtgaggggc cgattcacca tctccagagg caacgccaag    240
aacacggtat atctgcaaat gaacaatctg aaacctgagg acacggccgt ttactactgt    300
gcagccgact tcggtactag actacggttt acaactaatg actatcagta ctggggccag    360
gggacccagg tcaccgtctc ctca                                             384

<210> SEQ ID NO 48
<211> LENGTH: 369
<212> TYPE: DNA
<213> ORGANISM: Artificial
<220> FEATURE:
<223> OTHER INFORMATION: Nucleotide Sequence of Variable Region

<400> SEQUENCE: 48
gatgtacagc tggtggagtc tgggggagga ttggtgcagg ctggggactc tctgagactc       60
tcctgtgcgt actctggcgc aaccttcagt aacaatgtca tgggctggtt ccgccaggct     120
ccagggaggg cgcgtgactt tgtagcagca tttaacggtt ggagtagtgt tacagagtat    180
gcagactccg tgaagggccg attcttcgtc tccagagaca cgacaagag cacgatgtat    240
ctgcaaatga tcaacctcaa acccgacgac acggccgttt attttgtgc agcagggagg    300
cgttggcgtg caaatagga gactcactat gactactggg gccaggggac ccaggtcacc    360
gtctcctca                                                              369

<210> SEQ ID NO 49
<211> LENGTH: 372
<212> TYPE: DNA
<213> ORGANISM: Artificial
<220> FEATURE:
<223> OTHER INFORMATION: Nucleotide Sequence of Variable Region

<400> SEQUENCE: 49

| | | | | | |
|---|---|---|---|---|---|
| gatgtacagc | tggtggattc | tgggggagga | ttggtgcagc | ctgggggctc | tctgaccctc | 60 |
| tcctgtgtgc | tctctggacg | tcccttagt | tactatgccg | tgagctggtt | ccgccaggct | 120 |
| ccagggggg | agcgcgagtt | cgtagcagga | atttcgagga | gtggtggaag | tgtaaacttt | 180 |
| gcaggcttcg | tgaagggccg | attcaccgtc | tccagagaca | acgccaagag | cgcggtgaat | 240 |
| ctccaaatga | acagcctgaa | acgcgaggac | acggccgttt | attactgtgc | agccgatact | 300 |
| aatgtctatg | cctccgcgac | gttgtccaat | tatgcctatt | ggggccaggg | gacccaggtc | 360 |
| accgtctcct | ca | | | | | 372 |

<210> SEQ ID NO 50
<211> LENGTH: 372
<212> TYPE: DNA
<213> ORGANISM: Artificial
<220> FEATURE:
<223> OTHER INFORMATION: Nucleotide Sequence of Variable Region

<400> SEQUENCE: 50

| | | | | | |
|---|---|---|---|---|---|
| caggtaaagc | tggaggagtc | tgggggagga | ttggtgcagg | ctgggggctc | tctgagactc | 60 |
| tcctgtgcag | cctctggacg | caccttcagt | agttatcgct | tgggctggtt | ccgccaggct | 120 |
| ccagggaagg | agcgtgagtt | tgtagcagct | attagctgga | agatgatac | cacatactat | 180 |
| gcagactccg | tgaagggccg | attcaccatc | tccagagaca | acgccaagaa | cacggtgtat | 240 |
| ctacaaatga | acagcctgac | acctgaggac | tcggccgttt | attcttgtgc | agccaggggt | 300 |
| tatagtagat | cttggaaccc | gtggagcgag | tatgactact | ggggtcaggg | gacccgggtc | 360 |
| accgtctcct | ca | | | | | 372 |

<210> SEQ ID NO 51
<211> LENGTH: 363
<212> TYPE: DNA
<213> ORGANISM: Artificial
<220> FEATURE:
<223> OTHER INFORMATION: Nucleotide Sequence of Variable Region

<400> SEQUENCE: 51

| | | | | | |
|---|---|---|---|---|---|
| ggggtgcagc | tggtggagtc | tgggggaggt | tgggtgcagg | ctgggactc | tctgagactc | 60 |
| tcctgtacag | cctctggaag | cataccatat | gtccctgaca | tgcactggta | ccgccaggct | 120 |
| ccagggcaac | agcgccaatt | ggtcgcaact | attactcgtg | gaggcaacac | aatgtatgct | 180 |
| gactccgtga | agggccgatt | caccatctcc | agagacaacg | ccaagaacac | ggtatatcta | 240 |
| caaatgacct | ccctgaaacc | tgaggacacg | gccgtctact | actgtaatgc | agacgtttgg | 300 |
| tcgagtgttg | cattgaagct | tgtggaatac | tggggccagg | ggatccaggt | caccgtctcc | 360 |
| tca | | | | | | 363 |

<210> SEQ ID NO 52
<211> LENGTH: 363
<212> TYPE: DNA
<213> ORGANISM: Artificial
<220> FEATURE:

<223> OTHER INFORMATION: Nucleotide Sequence of Variable Region

<400> SEQUENCE: 52

```
caggtaaagc tggaggagtc tgggggaggg ttggtgcagg ctgggggtc tctgagactc    60
tcctgtgcag cctctggaag cataccatat gtccctgaca tgcactggta ccgccaggct   120
ccagggcaac agcgccaatt ggtcgcaact attactcgtg gaggcaacac aatgtatgct   180
gactccgtga agggccgatt caccatctcc agagacaacg ccaagaacac ggtatatcta   240
caaatgacct ccctgaaacc tgaggacacg gccgtctact actgtaatgc agacgtttgg   300
tcgagtgttg cattgaagct tgtggaatac tggggccagg ggatccaggt caccgtctcc   360
tca                                                                 363
```

<210> SEQ ID NO 53
<211> LENGTH: 369
<212> TYPE: DNA
<213> ORGANISM: Artificial
<220> FEATURE:
<223> OTHER INFORMATION: Nucleotide Sequence of Variable Region

<400> SEQUENCE: 53

```
caggtacagc tggtggagtc tgggggagga ttggtgcagg ctgggggctc tctgagactc    60
tcctgtacag actctgggcg caccttcggt gcttataaca tgggctggtt ccgccaggct   120
ccagggaagg agcgtgagtt tgtagcagct attaactgga gtggtattag tacatactat   180
acagactccg tgaagggccg attcactatc tccagagaca cgccaagaa cacggtgtgt    240
ctgcaaatga acaacctgag ccctgaggac acggccgttt attactgtgc agcaaatcgg   300
ggtggtaatt acgaaaaggt ctatctctac aacaactggg gccagggac ccaggtcacc    360
gtctcctca                                                           369
```

<210> SEQ ID NO 54
<211> LENGTH: 369
<212> TYPE: DNA
<213> ORGANISM: Artificial
<220> FEATURE:
<223> OTHER INFORMATION: Nucleotide Sequence of Variable Region

<400> SEQUENCE: 54

```
caggtacagc tggtggagtc tgggggagga ttggtgcagg ctgggggctc tctgagactc    60
tcctgtacag cctctgggcg caccttcggt gcttataaca tgggctggtt ccgccagact   120
ccagggaagg agcgtgagtt tgtagcagct attaactgga gtggtattag tacatactat   180
acagactccg tgaagggccg attcaccatc tccagagaca cgccaagaa cacggtgtat    240
ctgcaaatga acaacctgag ccctgaggac acggccgttt attactgtgc agcaaatcgg   300
ggtggtaatt acgaaaaggt ctatctctac aacaactggg gccagggac ccaggtcacc    360
gtctcctca                                                           369
```

<210> SEQ ID NO 55
<211> LENGTH: 375
<212> TYPE: DNA
<213> ORGANISM: Artificial
<220> FEATURE:
<223> OTHER INFORMATION: Nucleotide Sequence of Variable Region

<400> SEQUENCE: 55

```
gctgtgcagc tggtggagtc tgggggagga ttggtgcagg ctgggggctc tctgagactc    60
tcctgtgcag cctctggact caacttcagg acctatacca taggctggtt ccgccaggct   120
```

```
ccagggaagg agcgtgagtt tatagttggt attacttggg gtggtggtat catagactcc      180
atagactcca tgaagggccg cgccaccatc tccagagaca cgccgagaa cacggtgtat       240 ctgcaaatga acagcctgaa acctgaggac acggccgttt attcttgtgc agcaggcagg      300
aacacaggag gctacacacg actgtggcga agctatgact actggggcca ggggacccag      360
gtcaccgtct cctca                                                      375
```

```
<210> SEQ ID NO 56
<211> LENGTH: 363
<212> TYPE: DNA
<213> ORGANISM: Artificial
<220> FEATURE:
<223> OTHER INFORMATION: Nucleotide Sequence of Variable Region

<400> SEQUENCE: 56
caggtgcagc tggtggagtc tgggggaggg ttggtacagg ctgggggctc cctgagactc      60
tcctgtgcag cctctggacg cgcccccgag acctatgcca tggctggtt ccgtcaggct       120 ccagggaagg agcgtgagtt tgtagcgcat attattgtga ctggtgatag gacatactat      180
gcagactccg tgaagggccg attcaccatc tccagaaaca cgccaagaa cacggtgtat       240 ctgcaaatga acagcctgaa accggaggac acggccgttt attactgtgc agcagatcga     300
tcagcccgat gggaacctgg tacacactac tggggccagg gacccaggt caccgtctcc      360 tca                                                                    363
```

```
<210> SEQ ID NO 57
<211> LENGTH: 363
<212> TYPE: DNA
<213> ORGANISM: Artificial
<220> FEATURE:
<223> OTHER INFORMATION: Nucleotide Sequence of Variable Region

<400> SEQUENCE: 57
caggtaaagc tggaggagtc tgggggaggc ttggtgcagg ctgggggggtc tctgagactc     60 tcctgtgcag cctctggaag catctcacat gtccctaaca tgcactggta ccgtcaggct     120
ccgggtcaaa agcgccaatt ggtcgctact attactcgtg gaggcaacac aatgtatgca    180
gactccgtga agggccgatt caccatctcc agagagaacg ccaagaatac gatatatctg    240
caaatgacca ccctgaaacc tgaggacacg gccgtctact actgtaatgc agacgtttgg    300
tcgagtgctt tattcaaata cgtggagtac tggggccagg gacccaggt caccgtctcc     360 tca                                                                    363
```

```
<210> SEQ ID NO 58
<211> LENGTH: 366
<212> TYPE: DNA
<213> ORGANISM: Artificial
<220> FEATURE:
<223> OTHER INFORMATION: Nucleotide Sequence of Variable Region

<400> SEQUENCE: 58
caggtaaagc tggaggagtc tgggggagga ttggtgcagg ctggggactc tctgagactc     60
tcctgtacag cctctggcgg aacctacagt agcggtgtca tgggctggtt ccgccaggct    120
ccagggaagg agcgtgactt tgtagcatcg attaactgga gtggtgttac agactattca    180
gactccgtga agggccgatt cttcatctcc agagacaccg ccaagagcac ggtctatctg    240
cacatgttca gcctcaaagc cgacgacacg gccgtttatt tctgtgcagc agggagccgt   300
```

```
tggcgtgcaa atagtggtcg tcactatgac tactggggcc aggggaccca ggtcaccgtc    360
tcctca                                                                366
```

<210> SEQ ID NO 59
<211> LENGTH: 363
<212> TYPE: DNA
<213> ORGANISM: Artificial
<220> FEATURE:
<223> OTHER INFORMATION: Nucleotide Sequence of Variable Region

<400> SEQUENCE: 59

```
gaggtacagc tggtggattc tggggggaggc ttggtgcagg ctggggggtc tctgagactc     60
tcctgtgcag cctctggaag catctcatat gtccctgaca tgcactggta ccgccaggct    120
ccagggcaac agcgccaatt ggtcgcaact attactcgtg gaggcaacac aatgtatgca    180
gactccgtga agggccgatt caccatctcc agagacaacg ccaagaacac ggtatatctg    240
caaatgacct ccctgaaacc tgaggacacg gccgtgtact actgtaatgc agacgtttgg    300
tcgagtgttt tattcaaact tgtggagtac tggggccagg gacccaggt caccgtctcc    360 tca                                                                   363
```

<210> SEQ ID NO 60
<211> LENGTH: 232
<212> TYPE: PRT
<213> ORGANISM: Homo sapiens

<400> SEQUENCE: 60

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

225              230

<210> SEQ ID NO 61
<211> LENGTH: 498
<212> TYPE: DNA
<213> ORGANISM: Homo sapiens

<400> SEQUENCE: 61

```
gcacccatgg cagaaggagg agggcagaat catcacgaag tggtgaagtt catggatgtc    60
tatcagcgca gctactgcca tccaatcgag accctggtgg acatcttcca ggagtaccct   120
gatgagatcg agtacatctt caagccatcc tgtgtgcccc tgatgcgatg cgggggctgc   180
tgcaatgacg agggcctgga gtgtgtgccc actgaggagt ccaacatcac catgcagatt   240
atgcggatca acctcacca aggccagcac ataggagaga tgagcttcct acagcacaac   300
aaatgtgaat gcagaccaaa gaaagataga gcaagacaag aaaatccctg tgggccttgc   360
tcagagcgga gaaagcattt gtttgtacaa gatccgcaga cgtgtaaatg ttcctgcaaa   420
aacacagact cgcgttgcaa ggcgaggcag cttgagttaa cgaacgtac ttgcagatgt    480 gacaagccga ggcggtga                                                 498
```

<210> SEQ ID NO 62
<211> LENGTH: 165
<212> TYPE: PRT
<213> ORGANISM: Homo sapiens

<400> SEQUENCE: 62

```
Ala Pro Met Ala Glu Gly Gly Gln Asn His His Glu Val Val Lys
  1               5                  10                  15

Phe Met Asp Val Tyr Gln Arg Ser Tyr Cys His Pro Ile Glu Thr Leu
                 20                  25                  30

Val Asp Ile Phe Gln Glu Tyr Pro Asp Glu Ile Glu Tyr Ile Phe Lys
             35                  40                  45

Pro Ser Cys Val Pro Leu Met Arg Cys Gly Gly Cys Cys Asn Asp Glu
 50                  55                  60

Gly Leu Glu Cys Val Pro Thr Glu Glu Ser Asn Ile Thr Met Gln Ile
 65                  70                  75                  80

Met Arg Ile Lys Pro His Gln Gly Gln His Ile Gly Glu Met Ser Phe
                 85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
130                 135                 140

Arg Cys Lys Ala Arg Gln Leu Glu Leu Asn Glu Arg Thr Cys Arg Cys
145                 150                 155                 160

Asp Lys Pro Arg Arg
                165
```

<210> SEQ ID NO 63
<211> LENGTH: 45
<212> TYPE: DNA
<213> ORGANISM: Artificial
<220> FEATURE:
<223> OTHER INFORMATION: PCR primer VHHF1

<400> SEQUENCE: 63
gcccagccgg ccatggccsm bgtrcagctg gtggaktctg gggga    45

<210> SEQ ID NO 64
<211> LENGTH: 45
<212> TYPE: DNA
<213> ORGANISM: Artificial
<220> FEATURE:
<223> OTHER INFORMATION: PCR primer VHHF2

<400> SEQUENCE: 64
gcccagccgg ccatggccca ggtaaagctg gaggagtctg gggga    45

<210> SEQ ID NO 65
<211> LENGTH: 45
<212> TYPE: DNA
<213> ORGANISM: Artificial
<220> FEATURE:
<223> OTHER INFORMATION: PCR primer VHHF3

<400> SEQUENCE: 65
gcccagccgg ccatggccca ggctcaggta cagctggtgg agtct    45

<210> SEQ ID NO 66
<211> LENGTH: 41
<212> TYPE: DNA
<213> ORGANISM: Artificial
<220> FEATURE:
<223> OTHER INFORMATION: PCR primer VHHF4

<400> SEQUENCE: 66
gcccagccgg ccatggccga ggtgcagctg gtggagtgtg g    41

<210> SEQ ID NO 67
<211> LENGTH: 21
<212> TYPE: DNA
<213> ORGANISM: Artificial
<220> FEATURE:
<223> OTHER INFORMATION: PCR primer CH2R

<400> SEQUENCE: 67
cgccatcaag gtaccagttg a    21

<210> SEQ ID NO 68
<211> LENGTH: 29
<212> TYPE: DNA
<213> ORGANISM: Artificial
<220> FEATURE:
<223> OTHER INFORMATION: PCR primer CH2b3R

<400> SEQUENCE: 68
ggggtacctg tcatccacgg accagctga    29

<210> SEQ ID NO 69
<211> LENGTH: 34
<212> TYPE: DNA
<213> ORGANISM: Artificial
<220> FEATURE:
<223> OTHER INFORMATION: PCR primer VHHF

<400> SEQUENCE: 69
catgtgtaga ctcgcggccc agccggccat ggcc    34

<210> SEQ ID NO 70
<211> LENGTH: 47
<212> TYPE: DNA
<213> ORGANISM: Artificial

```
<220> FEATURE:
<223> OTHER INFORMATION: PCR primer VHHR

<400> SEQUENCE: 70
catgtgtaga ttcctggccg gcctggcctg aggagacggt gacctgg                47

<210> SEQ ID NO 71
<211> LENGTH: 42
<212> TYPE: DNA
<213> ORGANISM: Artificial
<220> FEATURE:
<223> OTHER INFORMATION: PCR primer VHHR

<400> SEQUENCE: 71
catgtgtaga ttcctgcggc cgctgaggag acggtgacct gg                    42
```

ANTI-VEGF ANTIBODY

RELATED APPLICATIONS

This application is a 35 U.S.C. § 371 national phase application of and claims priority, to PCT Application PCT/CN2015/070209 filed Jan. 6, 2015, the entire content of which is incorporated herein by reference in its entirety,

STATEMENT REGARDING ELECTRONIC FILING OF A SEQUENCE LISTING

A Sequence Listing in ASCII text format, submitted under 37 C.F.R. § 1.821, entitled 9363-31_ST25.txt, 35,746 bytes in size, generated on May 31, 2016 and filed via. EFS-Web, is provided in lieu of a paper copy. The Sequence Listing is incorporated herein by reference into the specification for its disclosures.

FIELD OF THE INVENTION

The present invention relates to antibodies and the uses thereof. In particular, the invention relates to antibodies which specifically bind vascular endothelial growth factor (VEGF), particularly heavy-chain antibodies, and more particularly single-domain antibodies; as well as a method of producing the antibodies and the therapeutic uses thereof.

BACKGROUND OF THE INVENTION

Angiogenesis refers to the new blood vessels formed from the development of pre-existing capillaries or post-capillary venules, which is a complex process involving many molecules of multiple cells. Angiogenesis is a complex process of coordination of angiogenic factors and inhibitory factors, when are in a state of balance under normal condition. The vascular system would be activated once the balance is broken, resulting in excessive angiogenesis or vascular degeneration by inhibition of the vascular system.

There are a number of diseases known to be associated with deregulated or undesired angiogenesis. Such diseases include, but are not limited to, tumors for example so-called solid tumors and liquid (or hematopoietic) tumors (e.g. leukemias and lymphomas), inflammatory diseases e.g. rheumatoid or rheumatic inflammation, especially arthritis (including rheumatoid arthritis), or other chronic inflammation e.g. chronic asthma, arteriosclerosis or post transplant arteriosclerosis, endometriosis, ocular neovascular diseases such as retinopathies (including diabetic retinopathy), age-related macular degeneration, psoriasis, hemangioblastoma, hemangioma, arteriosclerosis. Other diseases associated with deregulated or undesired angiogenesis will be apparent to those skilled in the art.

Vascular endothelial growth factor (VEGF), a heparin-binding growth factor specific for the vascular endothelial cell, may induce angiogenesis in vivo. It includes VEGF-A, VEGF-B, VEGF-C, VEGF-D, VEGF-E, VEGF-F and placental growth factor.

The main function of VEGF-A is to facilitate proliferation and migration of the vascular endothelial cell, and lumen formation, as well as to increase vascular leakage, promote the chemotaxis of monocytes and the formation of B cells. The biological effects of VEGF-A are mediated by the binding with its specific receptor, which mainly includes the specific receptors of vascular endothelial growth factor receptor 1 (VEGFR-1) and VEGFR-2. Moreover, VEGFR-2 is considered to be the major VEGFR, which exerts significant effect on proliferation of the vascular endothelial cell. VEGFR-2 induces, by intracellular kinase, VEGF to bind to the dimer and the receptors to be autophosphorylated, thereby enhancing cell mitosis (Klettner A, Roider J. Treating age-related macular degeneration interaction of VEGF-antagonists with their target. Mini Rev Med Chem, 2009, 9 (9): 1127-1135). VEGF-A comprising eight exons and seven introns is spliced into several isoforms during transcription, mainly including VEGF121, VEGF145, VEGF206, VEGF165 and VEGF189, which are of different molecular weight, solubility and heparin-binding capability. Among them, VEGF165 is the most predominant isoform of VEGF-A (Ferrara N, Gerber H P, Le Couter J. The biology of VEGF and its receptors, Nat Med. 2003, 9 (6): 669-676). VEGF165, which is a secreted soluble protein, directly acts on the vascular endothelial cell, thereby promoting cell proliferation, accelerating cell damage repair, increasing vascular permeability, reducing the intravascular thrombosis and occlusion of thrombus, and restraining intimal hyperplasia (Huang Chen-xing, Shen Zu-guang, Vascular endothelial growth factor—fundamental research and experimental study in plastic surgery, Chinese J Reparative and Reconstructive Surgery, 2002, 160: 64-68).

The existing drugs against vascular endothelial growth factor include Pegaptanib sodium (Macugen™), Ranibizumab (Lucentis™), Bevacizumab (Avastin™), VEGF Trap, etc. Currently, the controversy over anti-VEGF agents focuses on the possible exacerbation of the formation of tissue fibrous membranes. A major problem for the current anti-VEGF agents for the clinical treatment of various diseases (such as age-related macular degeneration) is that the agents have to be intraocularly injected frequently, thus inducing a potential risk for endophthalmitis. Researchers observed the effect of Bevacizumab and Macugen on different VEGF isoforms using the umbilical vein endothelial cell and Tenon fibrocyte. The results revealed that VEGF-165 and VEGF-121 mainly affect the angiogenesis, while VEGF-189 mainly affects the fibrogenesis process. Bevacizumab and Lucentis can inhibit all of the active isoforms of VEGF-A (Van Bergen T, Vandewalle E, Van de Veire S, et al. The role of different VEGF isoforms in scar formation after glaucoma filtration surgery. Exp Eye Res, 2011, 93: 689-699; and CATT research group, Martin D F, Maguire M G, et al. Ranibizumab and Bevacizumab for neovascular age-related macular degeneration. N Engl J Med, 2011. 364: 1897-1908), which might be the reason why Bevacizumab induced fibrosis of the vitreous cavity in some patients.

Currently, treatment using anti-VEGF agents has to be repeated every 4-6 week, while the annual average injection for Lucentis treatment in the $1^{st}$ year is about 6.9 times, and for Bevacizumab treatment, about 7.7 times (Li X, Hu Y, Sun X, Zhang J, Zhang M. Bevacizumab for neovascular age-related macular degeneration in China. Ophthalmology. 2012 October, 119(10): 2087-93). Due to the frequent intraocular injection, there is a potential risk for endophthalmitis. Consequently, the development of a novel antibody drug with long-lasting efficacy as well as better retinal absorption and permeability is urgently needed, so as to prolong the administration cycle and to reduce the discomfort and risk resulting from the injection in the patient.

In addition, the current techniques for expression and purification of anti-VEGF agents are complex, and in most cases entail high cost, poor stability and limited application.

A heavy chain antibody is an antibody isolated from the serum of a camel, which consists exclusively of heavy chains. Its antigen binding region is merely a single-domain connected to Fc region via a hinge region, and the antigen binding region still maintains the antigen binding function upon removal from the antibody. Thus the heavy chain antibody is also known as single domain antibody (sdAb) or nano antibody (nanobody). Unlike the conventional antibody, the single-domain antibody is a peptide chain of about 110 amino acids, with a molecular weight ⅒ of a conventional antibody, which provides a new way for the molecular construction of an antibody (Muyldermans, Single domain camel antibodies: current status. J Biotechnol 2001, 74:277-302). This type of single-domain antibody with a small molecule weight is heat-stable and also stable towards the detergent and high concentration of uric acid, with superior tissue permeability in vivo and enhanced solubility (Stanfield R, Dooley H, Flajnik M, Wilson I. Crystal structure of a shark single-domain antibody V region in complex with lysozyme. Science. 2004, 305 (5691)). The single-domain antibody facilitates expression and is suitable for expression in a prokaryotic system. The single-domain antibody is further characterized by, e.g., low production cost, unique antigen recognition epitope, and the capability of identifying hidden antigenic sites. As a result, the single-domain antibody plays an increasingly and unimaginably huge role in terms of immunological assay, diagnosis and treatment (Dirk Saerens, Gholamreza Hassanzadeh Ghassabeh, Serge Muyldermans. Single-domain antibodies as building blocks for novel therapeutics. Current Opinion in Pharmacology 2008, 8:600-608).

Therefore, an antibody which is able to overcome the above mentioned problems from the existing anti-VEGF agents is needed in the art, for example, a single domain antibody which can specifically bind VEGF and inhibit the activity thereof.

SUMMARY OF THE INVENTION

The present invention provides an anti-VEGF antibody and the variants or derivatives thereof, wherein the antibody comprises a heavy chain variable region, and wherein the heavy chain variable region comprises (i) CDR1, CDR2 and CDR3 as set forth in SEQ ID NO: 1, SEQ ID NO: 2 and SEQ ID NO: 3 respectively, or functional active variants thereof; or (ii) CDR1, CDR2 and CDR3 as set forth in SEQ ID NO: 4, SEQ ID NO: 5 and SEQ ID NO: 6 respectively, or functional active variants thereof; or (iii) CDR1, CDR2 and CDR3 as set forth in SEQ ID NO: 7, SEQ ID NO: 8 and SEQ ID NO: 9 respectively, or functional active variants thereof; or (iv) CDR1, CDR2 and CDR3 as set forth in SEQ ID NO: 10, SEQ ID NO: 11 and SEQ ID NO: 12 respectively, or functional active variants thereof; or (v) CDR1, CDR2 and CDR3 as set forth in SEQ ID NO: 13, SEQ ID NO: 14 and SEQ ID NO: 15 respectively, or functional active variants thereof; or (vi) CDR1, CDR2 and CDR3 as set forth in SEQ ID NO: 16, SEQ ID NO: 17 and SEQ ID NO: 18 respectively, or functional active variants thereof; or (vii) CDR1, CDR2 and CDR3 as set forth in SEQ ID NO: 19, SEQ ID NO: 20 and SEQ ID NO: 21 respectively, or functional active variants thereof; or (viii) CDR1, CDR2 and CDR3 as set forth in SEQ ID NO: 22, SEQ ID NO: 23 and SEQ ID NO: 24 respectively, or functional active variants thereof; or (ix) CDR1, CDR2 and CDR3 as set forth in SEQ ID NO: 25, SEQ ID NO: 26 and SEQ ID NO: 27 respectively, or functional active variants thereof; or (x) CDR1, CDR2 and CDR3 as set forth in SEQ ID NO: 28, SEQ ID NO: 29 and SEQ ID NO: 30 respectively, or functional active variants thereof; or (xi) CDR1, CDR2 and CDR3 as set forth in SEQ ID NO: 31, SEQ ID NO: 32 and SEQ ID NO: 33 respectively, or functional active variants thereof; said functional active variants are those which are at least 70%, 75%, 80%, 85%, 90%, 95%, 98% or 99% identical to the amino acid sequence from any one of SEQ ID NOs: 1-33.

In particular embodiments, the present invention provides heavy-chain antibodies consisting of heavy chains, wherein the variable region of the heavy chain, comprises: (i) CDR1, CDR2 and CDR3 as set forth in SEQ ID NO: 1, SEQ ID NO: 2 and SEQ ID NO: 3 respectively, or functional active variants thereof; or (ii) CDR1, CDR2 and CDR3 as set forth in SEQ ID NO: 4, SEQ ID NO: 5 and SEQ ID NO: 6 respectively, or functional active variants thereof; or (iii) CDR1, CDR2 and CDR3 as set forth in SEQ ID NO: 7, SEQ ID NO: 8 and SEQ ID NO: 9 respectively, or functional active variants thereof; or (iv) CDR1, CDR2 and CDR3 as set forth in SEQ ID NO: 10, SEQ ID NO: 11 and SEQ ID NO: 12 respectively, or functional active variants thereof; or (v) CDR1, CDR2 and CDR3 as set forth in SEQ ID NO: 13, SEQ ID NO: 14 and SEQ ID NO: 15 respectively, or functional active variants thereof; or (vi) CDR1, CDR2 and CDR3 as set forth in SEQ ID NO: 16, SEQ ID NO: 17 and SEQ ID NO: 18 respectively, or functional active variants thereof; or (vii) CDR1, CDR2 and CDR3 as set forth in SEQ ID NO: 19, SEQ ID NO: 20 and SEQ ID NO: 21 respectively, or functional active variants thereof; or (viii) CDR1, CDR2 and CDR3 as set forth in SEQ ID NO: 22, SEQ ID NO: 23 and SEQ ID NO: 24 respectively, or functional active variants thereof; or (ix) CDR1, CDR2 and CDR3 as set forth in SEQ ID NO: 25, SEQ ID NO: 26 and SEQ ID NO: 27 respectively, or functional active variants thereof; or (x) CDR1, CDR2 and CDR3 as set forth in SEQ ID NO: 28, SEQ ID NO: 29 and SEQ ID NO: 30 respectively, or functional active variants thereof; or (xi) CDR1, CDR2 and CDR3 as set forth in SEQ ID NO: 31, SEQ ID NO: 32 and SEQ ID NO: 33 respectively, or functional active variants thereof.

In one aspect, the heavy chain variable region of the antibody according to the present invention comprises at least one amino acid addition, insertion, deletion, and/or substitution. In another aspect, the antibody according to the present invention may be a monoclonal antibody, chimeric antibody or humanized antibody, multi-specific antibody and/or bispecific antibody as well as fragments thereof. In a particular embodiment, the antibody according to the present invention is humanized, In a particular embodiment, the heavy chain of the antibody according to the present invention may also comprise a constant region, in another embodiment, the heavy chain of the antibody according to the present invention also comprises an Fc fragment.

In certain embodiments, the antibody according to he present invention is a heavy-chain antibody, i.e. which consists exclusively of heavy chains. In certain embodiments, the antibody according to the present invention is a single-domain antibody.

In addition, the present invention provides an antibody which competes with a reference antibody for binding to VEGF, said reference antibody is any antibody as described above.

The present invention also relates to nucleic acid sequences encoding the antibodies mentioned above; vectors containing the nucleic acid sequence; and host cells, which express the antibody mentioned above, and/or comprise the nucleic acid sequence or vector.

The present invention also provides a method for producing antibodies, comprising the steps of culturing the above-mentioned host cells under the condition that allows the expression of the antibody; and purifying the antibody from the derived culture products.

The instant invention further relates to a pharmaceutical composition, comprising the antibody according to the present invention and a pharmaceutically acceptable excipient. The pharmaceutical composition may further comprise one or more therapeutically active compounds, e.g. the known anti-VEGF drugs or anti-tumor drugs.

In another aspect, the invention also relates to an antibody-drug conjugate (ADC), which comprises the antibody according to the present invention conjugated to other agents, e.g. chemotherapeutic agents, growth inhibitors, toxins (such as enzymatic activity toxins from bacteria, fungi, plant or animal origin, or fragments thereof) or radioisotopes (i.e. radioactive conjugates).

An antibody-drug conjugate may also comprise linkers between the drug unit and the antibody unit.

In addition, the present invention relates to a method for regulating VEGF activity by administering an effective amount of the anti-VEGF antibody according to the present invention. The invention relates to a method for inhibiting angiogenesis by administering to a patient in need thereof an effective amount of the antibody according to the present invention.

The present invention also provides a method for treating VEGF related diseases or disorders, comprising administering to a patient in need thereof an effective amount of at least one anti-VEGF antibody according to the present invention. The diseases or disorders include tumors or cancers or eye diseases. The tumors or cancers include breast cancer, brain tumors, renal carcinoma, ovarian carcinoma, thyroid carcinoma, lung cancer, colorectal cancer, endometrial cancer, angiosarcoma, bladder cancer, cancer of embryonic tissue, cervical tumor, malignant glioma, gastric cancer, pancreatic cancer and nasopharyngeal carcinoma, etc. The eye diseases include macular edemas resulting from various causes (including diabetic macular edema, macular edema after cataract operation or macular edema caused by various diseases e.g. uveitis), age-related macular degeneration, diabetic retinopathy, central retinal vein occlusion, neovascular glaucoma and other eye diseases involving neovascularization.

In addition, the present invention also relates to the use of the antibody according to the present invention in the preparation of a medicament for regulating VEGF activity; the use of the antibody according to the present invention in the preparation of a medicament for inhibiting angiogenesis; the use of the antibody according to the present invention in the preparation of a medicament for the treatment of VEGF-related diseases or disorders.

The present invention also provides a kit, which comprises a) the anti-VEGF antibody according to the present invention, or the pharmaceutical composition; and b) the instructions thereof.

BRIEF DESCRIPTION OF THE DRAWING

FIG. 1 shows an SDS-PAGE graph of the purified hVEGF165 protein. Lane 1 is a standard protein marker (Invitrogen, Cat. No.: LC5677); Lane 2 is 2 µg of non-reducing hVEGF165; Lane 3 is 5 µg of non-reducing hVEGF165; Lane 4 is 2 µg of reducing hVEGF165; Lane 5 is 5 µg of reducing hVEGF165.

FIG. 2 shows the result from the immunological assay, indicating a satisfactory immune response upon antigen injection to the animal, and the serum titer is approximately 1: 100 k.

FIG. 3 shows an agarose gel electrophoresis result of the total RNA, indicating that the quality of derived RNA met the requirement for library construction.

FIG. 4 shows the purification result by agarose gel electrophoresis of $V_HH$ fragments derived from PCR amplification following the reverse transcription of total RNA in FIG. 3 into cDNA.

FIG. 5 illustrates a phagemid vector for ligation of the $V_HH$ fragment.

FIG. 6 shows the determination of the fragment insertion rate of the phage display library. 72 randomly selected clones were detected by PCR, among which 69 clones were inserted with the single-domain antibody gene fragment, and thus the insertion rate was 69/72=95.8%.

FIG. 7 illustrates the sequence diversity determination of the single-domain antibody library obtained by sequencing the positive clones with inserted fragment in FIG. 6, and a satisfactory library diversity is demonstrated.

FIG. 8 illustrates a vector specialized for FASEBA screening. The ampicillin resistant vector, containing SASA and 6×His tag, can be used for secreted expression of the antibody.

FIGS. 9A-9C illustrate the antibody affinity ranking via FASEBA screening; 9A, 9B, and 9C display affinity ranking results from 3 different batches. The top-left: sensogram showing the binding and dissociation of different clones; the top-right: matrix digram showing binding and dissociation rates of different clones; the bottom-left: sensogram of different normalized clones; the bottom-right: sensogram of selected antibodies with high affinity.

FIGS. 10A and 10B show the result of the receptor competitive screening. Following the expression level screening and affinity ranking, 15 single-domain antibodies were selected for the screening. According to the competitive results compared with control, 7 superior clones were selected for the preparation of heavy-chain antibodies, and the cell proliferation inhibition assay.

FIG. 11 shows an inhibition curve of the heavy chain antibody on HUVEC cell proliferation. From the inhibition level on the cell proliferation by different concentrations of the antibody, it can be judged that 13 heavy-chain antibodies all showed inhibiting effect at varying degrees, among which A80887, A80723 and A69458 showed the greatest inhibition at the cellular level.

FIG. 12 shows the variable region sequences of the 13 heavy-chain antibodies in Example 11 (SEQ ID NOS: 34-46).

FIG. 13 is a schematic representation of the subintestinal vessels of the zebra fish. A certain period of time post administration, 15 zebra fish were randomly selected from each group and taken pictures under a fluorescent microscope, and then the quantitative analysis of the subintestinal vessels (SIVs) area was performed. Statistical analysis was performed with a T-test between two groups, and with a one-way ANOVA and Dunnett's T-test among more groups, in which p<0.05 indicates a statistically significant difference. The angiogenesis inhibiting efficiency can be calculated according to the following formula:

$$\text{Angiogenesis inhibition rate} = \left(1 - \frac{S \text{ (drug treatment group)}}{S \text{ (solvent group)}}\right) \times 100\%$$

FIG. 14 is a graph showing the area of the subintestinal vessels. As shown in the graph, like Avastin, A80887 displays significant inhibition on angiogenesis.

FIG. 15 is a graph showing the inhibition rate of the area of the subintestinal vessels, Avastin was used as the positive control. At the same molar mass (both were about 2.7 pmol), the angiogenesis inhibiting efficiency of A80887 was 23.2%, which was obviously better than 6.9% of Avastin (p<0.001). There is no statistical difference in terms of the angiogenesis inhibiting efficiency, compared with the administration of Avastin at a converted clinical dosage of 1 μg (6.7 pmol).

DETAILED DESCRIPTION

The present invention relates to antibodies which specifically bind VEGF, and variants or derivatives thereof; as well as a method of producing the antibodies and the therapeutic uses thereof. For example, the present invention relates to heavy-chain antibodies which specifically bind VEGF, and more particularly single-domain antibodies. Meanwhile, antibodies according to the present invention show better effects in inhibiting cell proliferation and angiogenesis than the prior-art anti-VEGF monoclonal antibody (e.g. Avastin), as further described in the following examples.

The single-domain antibody according to the present invention with a smaller molecular weight, generally 12-15 kD, compared with an Fab fragment and a full-length IgG antibody, can be used to build polyvalent antibody, and has an enhanced affinity, a prolonged half-life as well as extended dosing interval by genetic engineering. Compared with the ordinary antibody drugs, the antigen-binding affinity of single-domain antibodies is more stable under some extreme conditions such as at high temperature, in gastric acid and proteases etc, and single-domain antibodies have a high conformational stability. Different from the antibody drugs which prone to induce complement effects and cytotoxic responses, a single-domain antibody without Fc fragment, would not induce any complement effects. Meanwhile, due to its small molecular weight, the single-domain antibody shows better penetration when administered into ocular tissues and tumor tissues. It is feasible to administer the single-domain antibody orally or by other routes, due to the stability in an environment with protease, extreme temperatures and pH, as well as the high affinity thereof.

Single-domain antibodies can be expressed within prokaryotic or eukaryotic cells, such as *Escherichia coli* or yeast, on a large-scale, which is greatly beneficial for a large scale production and the control of production costs, as well as a good market prospect for the subsequent drug-development.

Unless otherwise defined herein, scientific and technical terms used in connection with the present invention shall have the meanings that are commonly understood by those of ordinary skill in the art.

The term "antibody" is well understood in biological and biomedical field and commonly refers to whole antibodies and any antibody fragment, or single chain thereof. Antibodies are glycoproteins secreted by specialized B lymphocytes known as plasma cells. They are also referred to as immunogobulins (Ig) because they contain a common structural domain found in many proteins. Antibodies most likely comprise two heavy (H) chains and two light (L) chains typically connected by disulfide bonds, or an antigen binding portion thereof. Each heavy chain is comprised of a heavy chain variable region ($V_H$) and a heavy chain constant region. Each light chain is also comprised of a variable region ($V_L$) and a constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). In certain embodiments, the antibody according to the present invention consists exclusively of heavy chains. In certain embodiments, the antibody according to the present invention is a single-domain antibody.

Complementarity determining regions (CDRs) and framework regions (FR) of a given antibody may be identified using the methods described by Kabat et al. in Sequences of Proteins of Immunological Interest, 5th Ed., US Dept. of Health and Human Services, PHS, NIH, NIH Publication no. 91-3242, 1991.

"Variants" of antibodies are encompassed by the present invention, for example, the heavy chain variable region of the antibody according to the present invention comprises at least one amino acid addition, insertion, deletion, and/or substitution; e.g. 10, 20, 30, 40, 50, and preferably e.g. 1, 2, 3, 4, 5, 6 7, 8, 9, 10 amino acid additions, insertions, deletions, and/or substitutions.

The instant invention also includes "derivatives" of antibodies. The "derivatives" of antibodies are chemically modified antibodies, for example by binding with other chemical portions such as polyethylene glycol, albumin (for example human serum albumin), phosphorylation and glycosylation. Unless otherwise specified, the term "antibody" includes the fragments, derivatives and variants thereof.

In one aspect, the present invention provides an anti-VEGF antibody and the variants or derivatives thereof, wherein the antibody comprises a heavy chain variable region, and wherein the heavy chain variable region comprises: (i) CDR1, CDR2 and CDR3 as set forth in SEQ ID NO: 1, SEQ ID NO: 2 and SEQ ID NO: 3 respectively, or functional active variants thereof; or (ii) CDR1, CDR2 and CDR3 as set forth in SEQ ID NO: 4, SEQ ID NO: 5 and SEQ ID NO: 6 respectively, or functional active variants thereof; or (iii) CDR1, CDR2 and CDR3 as set forth in SEQ ID NO: 7, SEQ ID NO: 8 and SEQ ID NO: 9 respectively, or functional active variants thereof; or (iv) CDR1, CDR2 and CDR3 as set forth in SEQ ID NO: 10, SEQ ID NO: 11 and SEQ ID NO: 12 respectively, or functional active variants thereof; or (v) CDR1, CDR2 and CDR3 as set forth in SEQ ID NO: 13, SEQ ID NO: 14 and SEQ ID NO: 15 respectively, or functional active variants thereof; or (vi) CDR1, CDR2 and CDR3 as set forth in SEQ ID NO: 16, SEQ ID NO: 17 and SEQ ID NO: 18 respectively, or functional active variants thereof; or (vii) CDR1, CDR2 and CDR3 as set forth in SEQ ID NO: 19, SEQ ID NO: 20 and SEQ ID NO: 21 respectively, or functional active variants thereof; or (viii) CDR1, CDR2 and CDR3 as set forth in SEQ ID NO: 22, SEQ ID NO: 23 and SEQ ID NO: 24 respectively, or functional active variants thereof; or (ix) CDR1, CDR2 and CDR3 as set forth in SEQ ID NO: 25, SEQ ID NO: 26 and SEQ ID NO: 27 respectively, or functional active variants thereof; or (x) CDR1, CDR2 and CDR3 as set forth in SEQ ID NO: 28, SEQ ID NO: 29 and SEQ ID NO: 30 respectively, or functional active variants thereof; or (xi) CDR1, CDR2 and CDR3 as set forth in SEQ ID NO: 31, SEQ ID NO: 32 and SEQ ID NO: 33 respectively, or functional active variants thereof.

The functional active variants are those which are at least 70%, e.g. at least 75%, at least 80%, at least 85%, at least 90%, e.g. 91%, 92%, 93%, 94%, 95%, 96%, 97%, 98%, 99% identical to the amino acid sequence from any one of SEQ ID NOs: 1-33.

In particular embodiments, the present invention provides heavy-chain antibodies consisting of heavy chains, and the variable region of the heavy chain comprises: (i) CDR1, CDR2 and CDR3 as set forth in SEQ ID NO: 1, SEQ ID NO: 2 and SEQ ID NO: 3 respectively, or functional active variants thereof; or (ii) CDR1, CDR2 and CDR3 as set forth in SEQ ID NO: 4, SEQ ID NO: 5 and SEQ ID NO: 6 respectively, or functional active variants thereof; or (iii) CDR1, CDR2 and CDR3 as set forth in SEQ ID NO: 7, SEQ ID NO: 8 and SEQ ID NO: 9 respectively, or functional active variants thereof; or (iv) CDR1, CDR2 and CDR3 as set forth in SEQ ID NO: 10, SEQ ID NO: 11 and SEQ ID NO: 12 respectively, or functional active variants thereof; or (v) CDR1, CDR2 and CDR3 as set forth in SEQ ID NO: 13, SEQ ID NO: 14 and SEQ ID NO: 15 respectively, or functional active variants thereof; or (vi) CDR1, CDR2 and CDR3 as set forth in SEQ ID NO: 16, SEQ ID NO: 17 and SEQ ID NO: 18 respectively, or functional active variants thereof; or (vii) CDR1, CDR2 and CDR3 as set forth in SEQ ID NO: 19, SEQ ID NO: 20 and SEQ ID NO: 21 respectively, or functional active variants thereof; or (viii) CDR1, CDR2 and CDR3 as set forth in SEQ ID NO: 22, SEQ ID NO: 23 and SEQ ID NO: 24 respectively, or functional active variants thereof; or (ix) CDR1, CDR2 and CDR3 as set forth in SEQ ID NO: 25, SEQ ID NO: 26 and SEQ ID NO: 27 respectively, or functional active variants thereof; or (x) CDR1, CDR2 and CDR3 as set forth in SEQ ID NO: 28, SEQ ID NO: 29 and SEQ ID NO: 30 respectively, or functional active variants thereof; or (xi) CDR1, CDR2 and CDR3 as set forth in SEQ ID NO: 31, SEQ ID NO: 32 and SEQ ID NO: 33 respectively, or functional active variants thereof.

In a specific embodiment, the heavy chain of the antibody according to the present invention may also comprise a constant region. In another specific embodiment, the heavy chain of the antibody according to the present invention also comprises an Fc fragment.

In certain embodiments, the antibody according to the present invention is a heavy-chain antibody, i.e. which consists exclusively of heavy chains. In certain embodiments, the antibody according to the present invention is a single-domain antibody.

In a more specific embodiment, the heavy chain of the antibody according to the present invention is set forth in SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45 or SEQ ID NO: 46.

In addition, the present invention also provides an antibody which competes with a reference antibody for binding to VEGF, said reference antibody is any antibody as described above.

The present invention also relates to nucleic acid sequences encoding the antibodies mentioned above; vectors containing the nucleic acid sequence; and host cells, which express the antibody mentioned above, and/or comprise the nucleic acid sequence or vector. The "host cells" are cells used for the expression of nucleic acids such as the nucleic acids according to the present invention. The host cells may be prokaryotes such as *Escherichia coli*, or eukaryotes such as unicellular eukaryotes (e.g., yeast).

In particular embodiments, the nucleic acid sequence is shown in SEQ ID NO: 47, SEQ ID NO: 48, SEQ ID NO: 49, SEQ ID NO: 50, SEQ ID NO: 51, SEQ ID NO: 52, SEQ ID NO; 53, SEQ ID NO: 54, SEQ ID NO: 55, SEQ ID NO: 56, SEQ ID NO: 57, SEQ ID NO: 58, or SEQ ID NO: 59, as elaborated in the embodiments below.

The present invention also provides a method for producing antibodies, comprising the steps of culturing the above-mentioned host cells under the condition that allows the expression of the antibody; and purifying the antibody from the derived culture products.

The instant invention further relates to pharmaceutical composition, comprising the antibody according to the present invention and a pharmaceutically acceptable excipient. The pharmaceutical composition may further comprise one or more therapeutically active compounds, e.g. the known anti-VEGF drugs or anti-tumor drugs, as elaborated in the embodiments below.

The therapeutically active compound may be administered with the antibody according to the present invention simultaneously or sequentially.

The pharmaceutical composition may be prepared as is known in the art. The term "excipient" generally refers to any component other than the active therapeutic ingredient(s). The excipient may be an inert substance, an inactive substance, and/or a not medicinally active substance. The excipient may serve various purposes, e.g. as a carrier, vehicle, diluent, tablet aid, and/or to improve administration, and/or absorption of the active substance. The formulation of pharmaceutically active ingredients with various excipients is known in the art, see e.g. Remington: The Science and Practice of Pharmacy (e.g. $19^{th}$ edition (1995), and any later editions). Non-limiting examples of excipients are: solvents, diluents, buffers, preservatives, tonicity regulating agents, chelating agents, and stabilizers.

The antibodies according to the present invention may be administered as pharmaceutical compositions. They may be prepared not only as liquid preparations e.g. injections, lyophilized formulations, aerosols etc., but also as solid preparations such as capsules. The route of administration may be, for example, through intravenous injection, oral or topical administration, such as transdermal, conjunctival and/or ocular, etc. In a particular embodiment, the route of administration is per oral. In another particular embodiment, the route of administration is per ocular.

In another aspect, the instant invention also relates to an antibody-drug conjugate, which comprises the antibody according to the present invention conjugated to other agents, e.g. chemotherapeutic agents, growth inhibitors, toxins (such as enzymatic activity toxins from bacteria, fungi, plant or animal origin, or fragments thereof) or radioisotopes (i.e. radioactive conjugates).

The local delivery of other agents using antibody drug conjugate can target the agents to tumor, while systemic administration of non-conjugated drugs may lead to an unacceptable cytotoxicity to normal cells as well as tumor cells to be removed.

An antibody-drug conjugate commonly comprises linkers between the drug unit and the antibody unit. In certain embodiments, the linkers may be cleaved within the cell, and thus cleavage of the linkers would induce release of the drug unit from the antibody in the intracellular environment. The linkers may be, for example, peptide-based linkers which may be cleaved by the intracellular peptidase or protease (including, but not limited to: lysosomes or inclusion-body proteinases). In certain embodiments, the length of the peptide-based linker is at least two amino acids or at least three amino acids. In a specific embodiment, the peptide-based linker which may be cleaved by the intracellular protease is a Val-Cit linker or a Phe-Lys linker.

In other embodiments wherein the linker may not be cleaved, the drug is released from for example the degradation of the antibody.

In addition, the present invention relates to a method for regulating (preferably inhibiting) VEGF activity and inhibiting mammalian angiogenesis by administering an effective amount of the anti-VEGF antibody according to the present invention.

In addition, the present invention relates to a method for regulating VEGF activity by administering an effective amount of the anti-VEGF antibody according to the present invention. The invention relates to a method for inhibiting angiogenesis by administering to a patient in need thereof an effective amount of the antibody according to the present invention.

The present invention also provides a method for the treatment of VEGF related diseases or disorders, comprising administering to a patient in need thereof an effective amount of at least one anti-VEGF antibody according to the present invention. The diseases or disorders include tumors or cancers or eye diseases. The tumors or cancers include breast cancer, brain tumor, renal carcinoma, ovarian carcinoma, thyroid carcinoma, lung cancer, colorectal cancer, endometrial cancer, angiosarcoma, bladder cancer, cancer of the embryonic tissue, cervical tumor, malignant glioma, gastric cancer, pancreatic cancer and nasopharyngeal carcinoma, etc. The eye diseases include macular edemas resulting from various causes (including diabetic macular edema, macular edema after cataract operation or macular edema caused by various diseases e.g. uveitis), age-related macular degeneration, diabetic retinopathy, central retinal vein occlusion, neovascular glaucoma and other eye diseases involving neovascularization.

The expression "a patient in need thereof" refers to any mammal, including such as, but not limited to, horse, cattle, cat, mouse, rabbit, rat, goat, etc. Preferably, the mammal is human.

For some therapeutic uses, various antibodies according to the present invention are administered in combination.

In addition, the present invention also relates to the use of the antibody according to the present invention in the preparation of a medicament for regulating VEGF activity; the use of the antibody according to the present invention in the preparation of a medicament for inhibiting angiogenesis; the use of the antibody according to the present invention in the preparation of a medicament for the treatment of VEGF-related diseases or disorders.

The present invention also provides a kit, which comprises a) the anti-VEGF antibody according to the present invention, or the pharmaceutical composition; and b) the instructions thereof.

The present invention is further illustrated by reference to the following non-limiting Examples.

EXAMPLE 1

Antigen Preparation

The target antigen in this Example is human VEGF165 (Human vascular endothelial growth factor 165, hVEGF165) molecule (Park J E, Keller G A, Ferrara N. The vascular endothelial growth factor (VEGF) isoforms: differential deposition into the subepithelial extracellular matrix and bioactivity of extracellular matrix-bound VEGF, Mol Biol Cell. 1993 December, 4(12):1317-26; Gengrinovitch S, Greenberg S M, Cohen T, Gitay-Goren H, Rockwell P, Maione T E, Levi B Z, Neufeld G. Platelet factor-4 inhibits the mitogenic activity of VEGF121 and VEGF165 using several concurrent mechanisms. J Biol Chem. 1995 Jun. 23; 270(25):15059-65; and Keyt B A, Berleau L T, Nguyen H V, Chen H, Heinsohn H, Vandlen R, Ferrara N. The carboxyl-terminal domain (111-165) of vascular endothelial growth factor is critical for its mitogenic potency. J Biol Chem. 1996 Mar. 29: 271(13):7788-95), wherein the nucleic acid sequence of human VEGF165 antigen is set forth in SEQ ID NO: 61; the amino acid sequence of human VEGF165 antigen is set forth in SEQ ID NO: 62.

Codons were optimized for mammalian expression according to the amino acid sequence. The optimized DNA obtained by total gene synthesis was cloned into eukaryotic expression vector pTT5 (authorized by the institution NRC) for the preparation of transfection plasmid. HEK293E cells were cultured for 7 days post transfection and collected by centrifugation. The supernatant was used for a two-step ion-exchange purification with manually assembled Capto column and HiTrap™ Q HP, wherein the endotoxin was removed. The protein concentration was determined using absorbance at $UV_{280\ nm}$; the level of protein endotoxin was detected by LAL method; and antigen activity was determined by HUVEC cell proliferation assay. The hVEGF165 protein was obtained at a concentration of 1.25 mg/ml, a volume of 22 ml, and a total amount of 27.5 mg, with an endotoxin level of 0.537 EU/ml (Table 1). SDS-PAGE results are shown in FIG. 1, and the protein was stored at −80° C.

TABLE 1

Purified hVEGF165 protein

| Protein | Volume (ml) | Concentration (mg/ml) | Total Amount (mg) | Endotoxin (EU/ml) |
|---|---|---|---|---|
| hVEGF165 | 22 | 1.25 | 27.5 | 0.537 |

EXAMPLE 2

Animal Immunization and Immune Response Testing

1. Animal Immunization

Alpaca (*Lama pacos*) was selected as the experimental animal, and six point injections were performed in the scapular and back regions respectively, at four different time points. The antigen was diluted in PBS, and the volume for each immunization was 1 ml. Information in connection with the amount of antigen and the adjuvant is shown in Table 2. BSA was included in the immunological reagent with a final concentration of 1 mg/ml. The antigen and adjuvant were freshly prepared and mixed before injection.

TABLE 2

Antigen information for Alpaca immunization

| | | Injection time | | | | |
|---|---|---|---|---|---|---|
| | | First time | Second time | Third time | Fourth time | Fifth time (optional) |
| Injection | Antigen concentration (μg/ml) | 100 | 50 | 50 | 10 | 10 |
| Adjuvant | Adjuvant type | FCA | FIA | FIA | PBS | FIA |
| | Volume (ml) | 1 | 1 | 1 | 1 | 1 |

The immunization scheme (Table 3) was designed to collect blood from jugular vein at four different time points, and anticoagulant was added during the blood collection. The first collection was 5 ml, and the remaining three collections were each 15 ml. Upon density gradient centrifugation using Ficoll 1.077 reagent (Sangon, Cat. No.: F760014-100) and anticoagulant, peripheral blood lymphocytes were isolated and resuspended for cell counting. With the addition of RNAlater (TIANGEN, Cat. No.: D P408-02), cells were stored at −20° C. Sera obtained from the gradient centrifugation were stored at −20° C. as well.

TABLE 3

Alpaca immunization schedule

| Day | Date | Manipulation |
|---|---|---|
| Day 0 | 2010 Oct. 11 | 5 ml peripheral blood was taken, primary immunization |
| Day 28 | 2010 Nov. 8 | the first booster injection |
| Day 49 | 2010 Nov. 29 | the second booster injection |
| Day 56 | 2010 Dec. 6 | 15 ml peripheral blood was taken |
| Day 70 | 2010 Dec. 20 | the third booster injection |
| Day 73 | 2010 Dec. 23 | 15 ml peripheral blood was taken |
| Day 77 | 2010 Dec. 27 | 15 ml peripheral blood was taken |

2. Immune Response Testing

Antigen specific immune response of the pre-immune serum sample and serum sample obtained upon the third and fourth injections were tested by enzyme-linked immunosorbent assay (ELISA). The immunogen was diluted with NaHCO$_3$ (pH 9.6) solution, and the microwell plate (Corning, Cat. No.: 9018) was coated at 4° C. overnight. The microwell plate was washed 4 times in a plate-washing machine with PBS-T solution, and blocked with 3% BSA blocking solution at 37° C. for 2 h. The microwell plate was washed four times with PBS-T solution, then the serum from gradient dilution was incubated at 37° C. overnight. The microwell plate was washed four times with PBS-T solution, then incubated with the horseradish peroxidase (HRP) conjugated goat anti-llama IgG secondary antibody (Novas Biologicals, Cat. No.: NB7242). TMB was used for development for 10 min, then 1M HCl was added to stop the reaction. The reaction system upon termination of the reaction was detected for absorbance at 450 nm using MK3 (Thermo) microplate reader. It can be concluded from the ELISA results, that a satisfactory immune response was induced upon antigen injection to the animal, with the serum titer of 1: 100 k (FIG. 2).

EXAMPLE 3

Antibody Phage Library Construction 3.1. RNA Isolation

TRIzol reagent was added into the isolated peripheral blood lymphocytes at a volume according to the corresponding cell number. Upon cell lysis, the isolation and extraction of total RNA were carried out following the instruction of TRIzol® Plus RNA purification system (Invitrogen, Cat. No.: 12183-555). Quality of the total RNA was determined by agarose gel electrophoresis, and RNA concentration was measured by light absorption method. According to the measurements, 105.6 µg total RNA was obtained. RNA showed an intact morphology in the agarose gel electrophoresis (FIG. 3), which met the requirements for the library construction.

3.2. Reverse Transcription PCR

Total RNA was reverse transcribed into cDNA using an Oligo(dT) 20 primer according to the instruction of SuperScript™ III First-Strand Synthesis System (Invitrogen, Cat. No.: 18080-051). According to the sequence feature of the camel antibody, specific forward primers and reverse primers were selected for the amplification of VHH (A. Bell et al., Differential tumor-targeting abilities of three single-domain antibody formats, Cancer Lett. 2010 Mar. 1; 289(1): 81-90; and Honda Toshio, Akahori, Yasushi, Kurosawa Yoshikazu. Methods of constructing camel antibody libraries. United States Patent 2005/0037421 A1), and the primer sequences are specified in Table 4. Fragments containing VHH segment of approximately 600 bp were isolated and purified according to the molecular weights of PCR products through the first round of cDNA PCR, then the VHH fragments were obtained through the second round of PCR amplification. Two Sfi I restriction enzyme sites for different recognition sequences were simultaneously introduced at both ends of the DNA fragment, and a total of 101 µg gel-purified VHH fragments (FIG. 4) were thus obtained.

TABLE 4

Primer sequences and PCR amplification

| Name | Sequence (5'-3') | Function |
|---|---|---|
| VHHF1 (SEQ ID NO: 63) | GCCCAGCCGGCCATGGCCSMBGTRCAGCT GGTGGAKTCTGGGGGA | Forward primer in the first amplification cycle |
| VHHF2 (SEQ ID NO: 64) | GCCCAGCCGGCCATGGCCCAGGTAAAGCTG GAGGAGTCTGGGGGA | Forward primer in the first amplification cycle |
| VHHF3 (SEQ ID NO: 65) | GCCCAGCCGGCCATGGCCCAGGCTCAGGT ACAGCTGGTGGAGTCT | Forward primer in the first amplification cycle |
| VHHF4 (SEQ ID NO: 66) | GCCCAGCCGGCCATGGCCGAGGTGCAGCT GGTGGAGTGTGG | Forward primer in the first amplification cycle |
| CH2R (SEQ ID NO: 67) | CGCCATCAAGGTACCAGTTGA | Reverse primer in the first amplification cycle |
| CH2b3R (SEQ ID NO: 68) | GGGGTACCTGTGATCCACGGACCAGCTGA | Reverse primer in the first amplification cycle |
| VHHF (SEQ ID NO: 69) | CATGTGTAGACTCGCGGCCCAGCCGGCCATGGCC | Forward primer in the second amplification cycle, introducing restriction sites |
| VHHR (SEQ ID NO: 70) | CATGTGTAGATTCCTGGCCGGCCTGGCCTG AGGAGACGGTGACCTGG | Reverse primer in the second amplification cycle, introducing restriction sites |

TABLE 4-continued

Primer sequences and PCR amplification

| Name | Sequence (5'-3') | Function |
|---|---|---|
| VHHR (SEQ ID NO: 71) | CATGTGTAGATTCCTGCGGCCGCTGAGGAGACGGTGACCTGG | Reverse primer in the second amplification cycle, introducing restriction sites |

3.3 Library Construction $V_HH$ fragments amplified from different primers using different batches of cells were mixed, and then digested with Sfi I restriction enzyme. The $V_HH$ fragments were separated by 2% agarose gel electrophoresis and purified, and the digested $V_HH$ was thus obtained; meanwhile, phagemid vector (FIG. 5) was digested with Sfi I restriction enzyme, separated by 1.5% agarose gel electrophoresis and purified, and the digested vector was thus obtained. The concentration of digested $V_HH$ and phagemid vector was determined by absorption spectrophotometry. Subsequently, the vector was mixed with the fragment at a molar ratio of 1:3, 1:5, 1:10 vector/fragment respectively followed by the addition of T4 ligase (NEB, Cat. No.: M0202L), and thus the ligation reaction system of equal volume was prepared. The ligation was performed at 16° C. overnight. The extraction with phenol/chloroform, extraction with chloroform and precipitation with ethanol were sequentially performed on the ligation system, and then the concentration of the purified ligation products were determined by absorption spectrophotometry. Electrotransformation was performed for the products obtained from three different ligation systems with equal amount of DNA and by TG1 competent coils. The size of the library from three ligation systems, i.e. the transformation efficiency was calculated by plating and gradient dilution method. Positive clones were randomly selected and sent for the library diversity test. A reaction system with the highest transformation efficiency was chosen for a large scale ligation and transformation, and the capacity of the library was calculated. According to the results from plate counting, the capacity of the library was approximately $1.8 \times 10^8$ (Table 5).

TABLE 5

Capacity calculation for a single-domain antibody phage display library

| Dilution | Capacity-A | Capacity-B |
|---|---|---|
| $10^{-2}$ | 1920 | 2800 |
| $10^{-3}$ | 760 | 680 |
| $10^{-4}$ | 58 | 57 |
| $10^{-5}$ | 5 | 9 |

A random cloning PCR was performed on the library colony, and it can be seen that the insertion rate of the fragment in the library was 95.8% (FIG. 6). The positive clones with inserted fragment were then sequenced, and a satisfactory library diversity was demonstrated through alignment of amino acid sequences of the CDR regions in single-domain antibodies (FIG. 7). Following plating overnight, the bacteria were collected with 2YT culture medium containing 100 μg/ml ampicillin and 2% glucose, and then centrifuged at 5,000 g to remove cell metabolites. A duplicate of the cells was resuspended in the same culture medium for library storage.

EXAMPLE 4

Phage Display and Screening 4.1. Preparation of Biotinylated Antigen Complex

The HVEGF165 protein was biotinylated according to the instruction of EZ-Link Sulfo-NHS-LC-Biotinylation Kit (Pierce, Cat. No.: 21335). HABA assay was used for the detection of biotinylation level of the protein. The biotinylated hVEGF165 was mixed with 0.5 ml M-280 streptavidin beads (Invitrogen, Cat. No.: 112.06D), and incubated at 4° C. overnight. Then the beads were separated by a magnetic rack. The biotinylated protein which did not bind to the beads was eluted with PBS solution, and was further used for the preparation of bead coupled antigen complex. 0.52 mg hVEGF165 protein was obtained following the biotinylation and purification, and the biotinylation level detected by HABA assay was 6 mole biotin molecules per mole protein.

4.2. Phage Library Recovery

Approximately 100 μl (MOI was approximately 20) phage library stock was inoculated into 2YT medium, and incubated at 225 rpm, 30° C. M13KO7 helper phage (NEB, Cat. No.: N0315S) was added during logarithmic growth phase ($OD_{600}=0.5$), incubated at 225 rpm, 30° C. overnight. Phages were collected by centrifugation, and the culture supernatant was mixed with PEG/NaCl solution and then centrifuged for the phage pellet. Finally, pellets of the recovered phages were suspended in 1-2 ml PBS following multiple centrifugations and resuspensions. The titer of the recovered phage library was calculated by limited gradient dilution, and thus a library of $3.15 \times 10^{13}$ pfu/ml was obtained.

4.3. Phage Screening Against the Target Protein

Phages of $\sim 2 \times 10^{11}$ pfu were taken as the first round input, incubated with 10 ul of antigen-magnetic bead complex at room temperature, and mixed mildly in a rotator for 2 hours; magnetic beads were separated by a magnetic rack. The phages which did not bind to the magnetic beads were washed off. Resuspension of the magnetic beads and elution of the non-specific binding should be performed 7 times. Beads in the last resuspension were added into TEA solution. Phages binding to the antigen-bead complex were eluted and separated, and immediately neutralized by adding Tris-HCl buffer. The phage output from the first round screening was calculated by limited gradient dilution, while phages obtained in the first round elution were incubated overnight and amplified. The detailed parameters and procedures were the same as described above for the library recovery. The library amplified from $\sim 10^{11}$ pfu output obtained in the first round screening was used as the second round input, and was incubated and screened with 1 ul antigen-bead complex. The detailed parameters and procedures were the same as in the first round screening.

4.4. Phage ELISA Identification

Single clone plaque was selected from the overnight plate used for the calculation of output in the second round screening, inoculated into a 96-deep well plate with 500 μl of 2YT medium in each well, and incubated at 225 rpm, 30° C. At the logarithmic growth phase ($OD_{600}=0.5$) M13KO7 helper phage (NEB, Cat. No.: N0315S) was added, and the culture was incubated at 225 rpm, 30° C. overnight. The bacteria were collected by centrifugation, and then the obtained supernatant was added into a microwell plate which pre-coated with hVEGF165 and blocked. HPR/anti-M13 monoclonal antibody (GE Healthcare, Cat. No.: 27-9421-01) was used as the secondary antibody for detection, while other parameters for ELISA were the same as the immune response testing above. The positive rate of output was evaluated from the light absorbance. Some randomly selected positive phage clones with antigen recognition were subject to $V_HH$ fragment sequencing, and the diversity of clones derived from phage display was inferred from sequence alignment and analysis. Whether more rounds of phage display screening were required may be determined according to the positive rate and sequence diversity. The positive phage clone was more than 50%, and met the requirement for diversity. Therefore, phages obtained from the second round of screening were selected for sdAb gene cloning and FASEBA library construction, thereby allowing for further clonal screening.

TABLE 6

Phage panning and ELISA assay

| Round Number | Input (pfu) | Output (pfu) | Output/Input ration | Enrichment | Phage ELISA Positive rate |
|---|---|---|---|---|---|
| 1 | 2 * 10^11 | 6.19 * 10^5 | 3.095 × 10−6 | 1 | 16.3% |
| 2 | 10^11 | 1.35 * 109 | 1.35 × 10−2 | 4361 | 56.5% |

EXAMPLE 5

FASEBA Screening 5.1. FASEBA Library Construction

Phage DNAs obtained from the last round of phage display were extracted. The fragment encoding $V_HH$ was amplified by PCR, and cloned into a patented FASEBA vector by ligation. As such, the overall structure of the constructed clone was $V_HH$-linker-SASA-6×His (FIG. 8). The ligation product will be transformed into the TG1 cells.

5.2. FASEBA Screening 5.2.1. Sample Preparation and Evaluation of the Expression Level Single clones were randomly picked from the constructed FASEBA library, and put into a 96-deep well plate with 500 μl 2YT medium in each well. When the culture reached $OD_{600}$ of 0.6-0.8, IPTG was added to induce the expression overnight. The bacteria were collected by centrifugation, and added into a microwell plate which was pre-coated with BSA and blocked after removal of 100 μl supernatant, HPR-labeled mouse anti-His monoclonal antibody (GenScript, Cat. No.: A00186) was used as the secondary antibody for detection. Meanwhile, an aliquot of the supernatant was added into a microwell plate which was precoated with hVEGF165 protein and blocked. HPR-labeled mouse anti-His monoclonal antibody (GenScript, Cat. No.: A00186) was used as the secondary antibody for detection. $OD_{450}$ absorbance was used for the evaluation of the expression level of different clones. Over 5,000 clones in total from different batches were screened for expression level and antigen-binding capacity, and 138 positive clones with a relative higher expression and a higher antigen-binding capacity were selected for affinity ranking and subsequent screenings.

5.2.2. Chip Preparation

According to the BIAcore T200 instrument manual, BSA was immobilized on the CM5 chip surface by the standard coupling procedure (GE Healthcare, Cat. No.: BR-1006-68). The basic process was as follows: HBS-EP solution (0.01M HEPES [pH 7.4], 0.15M NaCl, 3 mM EDTA and 0.005% [v/v] surfactant P20) was used as the running buffer for the instrument at 25° C. with a flow rate of 10 ml/min. Firstly, 0.4 M N-ethyl-N'-(3-dimethylaminopropyl)-carbodiimide hydrochloride (EDC)/0.1M N-hydroxysuccinimide (NHS) (1:1) was injected for more than 7 minutes to activate the carboxymethyl dextran surface. Then 20 μg/ml BSA protein solution diluted in 10 mM acetate sodium (pH 4.5) was injected for 7 minutes, and finally 1M aminoethanol (pH 8.5) was injected for 7 minutes to block the unbound active sites. Following such procedure, the obtained level of BSA coupling reaction was 327 resonance units (RU).

5.2.3. Affinity Ranking of Anti-hVEGF165 Single-Domain Antibodies

The aforementioned supernatant by SdAb-SASA cloning and expression was filtrated through a 96-well filter plate (Pall, Cat. No.: PN5045) via centrifugation at 4000 g, 4° C. for 5 minutes to remove the bacteria and other particles. sdAb to be detected was diluted by HBS-EP solution and then flowed through the BSA coupled chip surface sequentially. Ranking analysis procedure comprised the following four steps:

a. Chips for BSA immobilization were used to capture the SASA coupled single-domain antibody; b. hVEGF165 was injected, so as to allow it to bind at the surface of chip which captured a single domain antibody; c. Running buffer was injected, and dissociation phase were monitored for 300 s; d. BSA coupled chip surface was regenerated by injecting 10 mM glycine/HCl (pH 2.0), at 30 ul/min, for 30 s. Surface regeneration was required for BSA chips following each round of antibody capture, antigen binding and antigen dissociation. Purified SASA protein solution at a concentration of 200 nM flowing over the BSA chip surface was used as a control for the regeneration effect. Rankings of the 138 clones were performed in 3 batches, and clone A10981 was used as a control. There was a satisfactory consistency among six A10981 parallel clones in different batches, and the dissociation rate was approximately 20% within 400 s. 93 clones had a lower dissociation rate compared to A10981 (FIGS. 9A-9C), and were picked up for sequencing. 53 single-domain antibodies were selected for prokaryotic expression, and were tested by cell proliferation inhibition assay. 15 single-domain antibodies were used for a further competitive screening.

5.2.4. Competitive Screening of hVEGFR2

Following the expression level screening and affinity ranking, 15 single-domain antibodies were selected for the receptor competitive screening, in order to obtain an antibody which can block antigen hVEGF165 and the binding of the receptor hVEGFR thereof. Detailed procedure was as follows:

a. hVEGFR2 protein was immobilized on the CM5 chip surface by the amino coupling method (see 5.2.2); b. hVEGF165 protein was injected, and the binding profile thereof was observed. The injection stopped when the binding profile came near to saturation; c. Different single-domain antibodies were injected at the surface of the hVEGF165-bound chip and binding profile thereof was observed. Meanwhile the commercial available anti-VEGF drug Avastin was injected as the control; d. If the epitope at which an antibody binds to VEGF165 is just the binding site between VEGF and VEGFR2, then the antibody will no longer bind to VEGF, or will compete with the VEGF which already binds to VEGFR2. As such, the binding signal will be significantly lower than VEGF itself. If the epitope at which an antibody binds to VEGF165 is different from or irrelevant to the binding site between VEGF and VEGFR2, then the antibody will bind to VEGF165 which was already bound to the receptor. As such, the resulting binding signal will be significantly higher than VEGF itself. According to the competitive results compared with the control (FIGS. 10A-10B), 7 superior clones were selected for the preparation of heavy-chain antibodies, and the cell proliferation inhibition assay.

EXAMPLE 6

Preparation of the Single-domain Antibody

The procedure for prokaryotic expression, purification of the single-domain antibody and endotoxin removal is set forth below.
6.1. Preparation of the Reagents
6.1.1. Reagents for Prokaryotic Expression
Tryptone, OXOID LP0042
Yeast extract, OXOID LP0021
Casein acid hydrolysate, Sigma C9386
$KH_2PO_4$, Sinopharm AR CAS [7778-77-0]
$Na_2HPO_4.12H_2O$, Sinopharm AR 10020318
$NH_4Cl$, Sinopharm AR CAS [12125-02-9]
NaCl, Sinopharm AR 10019318
$MgCl_2$, Sinopharm AR 7791-18-6
$CaCl_2$, Sinopharm AR 10043-52-4
Glucose, Sinopharm AR 10010518
Glycerol, Sigma G5516-500ML
IPTG, Amresco 0487-100G
VB1, Aladdin AR 1099302
 Ampicillin, 100 mg/ml, filtrated with 0.22 μm filter;
 IPTG stock solution: 1 M, filtrated with 0.22 μm filter, stored in 1-2 ml aliquots, cryopreserved at ~20° C. (valid for 3 months);
 $MgCl_2$ stock solution: 1 M, autoclaved at 121° C. for 30 min, stored in 1-2 ml aliquots, at 4° C. (valid for 6 months);
 $CaCl_2$ stock solution: 1 M, filtrated with 0.22 μm filter, stored in 1-2 ml aliquots, at 4° C. (valid for 6 months);
 VB1 stock solution: 50 mg/ml, filtrated with 0.22 μm filter, stored in 1-2 ml aliquots, at 4° C. (valid for 6 months);
 Glucose stock solution: 20% (W/V), filtrated with 0.22 μm filter, stored at 4° C. (valid for 3 months);
 Glycerol stock solution: 50% (V/V), autoclaved at 121° C. for 30 min, stored at 4° C. (valid for 6 months);
 Casein acid hydrolysate stock solution: 4%, autoclaved at 121° C. for 30 min, stored at room temperature (valid for 3 months);
 10×M9 salt solution: 6% $Na_2HPO_4$ (W/V), 3% $KH_2PO_4$ (W/V), 1% $NH_4Cl$ (W/V), 0.5%; NaCl (W/V), autoclaved at 121° C. for 30 min, stored at room temperature (valid for 3 months);
 2YT medium: 1.6% (W/V) Tryptone, 1.0% (W/V) yeast extract, 0.5% (W/V) NaCl, autoclaved at 121° C. for 30 min;
 10×TB medium: 12% (W/V) Tryptone, 24% (W/V) yeast extract, 4% (v/v) glycerol, autoclaved at 121 for 30 min.
6.1.2. Reagents and Equipments for Protein Purification
 10× BugBuster Protein Extraction Reagent (Novagen, 70921-4);
 100 mM PMSF: 1.74 g PMSF in 100 ml isopropanol solution (Beyotime Biotechnology, ST506);
 10 mg/ml nucleases (DNase I): typically 1 μl (Life Science Product and Service, DD0099-1) per gram wet weight of the bacteria cells;
 5 mg/ml lysozyme: typically 100 μl (Sunshinebio L0005-10) per gram wet weight of the bacteria cells;
 Quick Start™ Bradford reagent (Bio-Rad, 500-0204);
 High Affinity Ni-NTA Resin (GenScript, L00250);
 HiTrap™ Desalting, 5 ml, (GE Healthcare 17-1408-01);
 ÄKTA purifier 10 (GE Healthcare);
 Lysis buffer: 20 mM HEPES, 150 mM NaCl, 10% (V/V) glycerol, 40 mM imidazole, pH 8.0;
 Binding buffer: 20 mM $Na_2HPO_4$, 0.5 M NaCl, 20 mM imidazole, pH 7.4;
 Washing buffer: 20 mM $Na_2HPO_4$, 0.5 M NaCl, 40 mM imidazole, pH 7.4;
 Elution buffer: 20 mM $Na_2HPO_4$, 0.5 M NaCl, 300 mM imidazole, pH 7.4;
 1×PBS: 137 mM NaCl, 10 mM $Na_2HPO_4$, 2 mM $KH_2PO_4$, pH 7.4.
6.1.3. Reagents and Equipments for Endotoxin Removal
 ToxinEraser™ Endotoxin Removal Resin 1.5 ml resin (GenScript, L00402);
 PD-10 Columns; ToxinEraser™ Regeneration Buffer (GenScript, M01053);
 ToxinEraser™ Equilibration Buffer (GenScript M01054);
 Gel clot endotoxin assay kit (GenScript, L00451);
 Tachypleus Amebocyte Lysate (TAL for short, sensitivity of 0.25 EU/ml, Chinese Horseshoe Crab Manufactory, Co., Ltd., Xiamen, China);
 0.1 M NaOH (prepared by using nonpyrogenic water);
 0.1 M HCl (prepared by using nonpyrogenic water);
 37° C. constant temperature incubator.
6.1.4. Reagents and Equipments for Filtration Sterilization
 Millex-GP Filter Unit, 0.22 μm (Millipore, Lot: R4AA43868).
6.1.5. Reagents and Equipments for Protein Concentration Determination and Detection
 Nanodrop 2000 spectrophotometer (Thermo);
 ExpressPlus PAGE Gel: 4-20%, 12 wells (GenScript, M42012);
 MOPS Running Buffer Powder (GenScript, M00138);
 Loading Buffer (5×, Non-reducing): 0.25 M Tris-HCl (pH 6.8), 10% SDS, 0.5% bromophenol blue, 50% glycerol, 7.8% DTT;
 Loading Buffer (5×, reducing): 0.25 M Tris-HCl (pH 6.8), 10% SDS, 0.5% bromophenol blue, 50% glycerol.
6.2. Methods and Procedures
6.2.1. Strain Preparation
 a) Transformation: The plasmid for prokaryotic expression constructed with single-domain antibody gene was transformed into TG1 cells by chemical transformation or electroporation. The cells were spread onto the plate containing ampicillin-resistant 2YT medium, and incubated at 37° C. overnight;
 b) Single clone selection: Ampicillin at a final concentration of 200 μg/ml and 2% (W/V) glucose were added into 10 ml 2YT medium. The tweezer was cauterized thoroughly on an alcohol lamp, cooled down, and used for picking up 10 μl sterilized pipette tip. A single clone was selected from the transformation plate and inoculated into the medium, incubated at 225 rpm, 37° C. overnight.
6.2.2. Transfer and Induction
 a) Preparation of M9 medium: Glucose at a final concentration of 0.2% (W/V), 1 mM $MgCl_2$, 0.1 mM $CaCl_2$, 0.4% (W/V) Casein acid hydrolysate, 5 mg/L VB1 and 200 μg/ml ampicillin were added into 1×M9 salt solution, and the resulting solution was preheated in a shaker at 37° C.;

b) Transfer: The overnight culture was removed from the shaker, transferred at a 1:100 transfer system, centrifuged for 10 min at 4000 rpm, resuspended in fresh 1×M9 salt solution, centrifuged at 4000 rpm for 10 min, resuspended again and transferred into a preheated medium, then placed in a shaker and incubated at 37° C., at 225 rpm, for 24 h;

c) Induction: Additional 1×TB medium, IPTG at a final concentration of 1 mM and ampicillin at a final concentration of 200 µg/ml were added into M9 medium. The cells were incubated at 225 rpm, 25° C. for 48 h (ampicillin at a final concentration of 200 µg/ml was added again at 24 h);

d) Sample collection: At the end of the induction, the overnight culture in aliquots was dispensed into centrifuge tubes, centrifuged at 4° C., 11,000 rpm, for 15 min, and the bacteria cells were collected.

6.2.3. Protein Purification a) Sample Preparation by BugBuster Lysis Method i. Lysis: The pellets were resuspended in 5 ml Lysis buffer per gram wet weight of the *E. coli* cells (Lysis buffer: 10× BugBuster Protein Extraction Reagent was diluted with binding buffer to 1×; lysozyme at a final concentration of 100 µg/ml, nuclease at a final concentration of 2 µg/ml and 1 mM PMSF were added), and incubated for 1 h at room temperature under medium-speed shaking.

ii. Preparation of protein crude extract: The lysed samples were centrifuged at 4° C., 12,000 g for 30 min, and then the supernatant was collected and filtrated with a 0.22 µm filter.

b) Purification by Ni-Colum Affinity Chromatography i. Column Equilibration: 5 column volumes of ddH$_2$O and equilibration buffer were used for the equilibration of High Affinity Ni-NTA Resin;

ii. Binding: The protein crude extract was mixed with an appropriate amount of High Affinity Ni-NTA Resin, and incubated while shaking for 1 h. After incubation, the mixture of the crude extract and column packings was added into an empty PD-10 column to collect column packings, and the effluent was collected for subsequent analysis;

iii. Washing: The protein impurities were eluted using at least 50 column volumes of washing buffer. (Bradford staining solution was used as an indicator during the Washing step: 5 µl washing solution was added into 200 µl Bradford staining solution. If the color turned blue, then the washing of protein impurities continued until the color of the staining solution remained essentially unchanged. Then proceeded to the next step);

iv. Elution: The target protein was eluted using at least 10 column volumes of Elution Buffer. (Bradford staining solution was used as an indicator of a complete elution during the Elution step, and the procedure was the same as step iii).

c) Desalination/Buffer Exchange i. Equilibration: 5 column volumes of ddH$_2$O and PBS were used for the equilibration of a 5 ml HiTrap™ Desalting column on an ÄKTA purifier 10 system at an appropriate flow rate (0.5 mL/min);

ii. Sample loading: An appropriate amount of protein solution (0.5 mL) purified by Ni-affinity chromatography was introduced into the HiTrap™ Desalting column at an appropriate flow rate (0.5 mL/min);

iii. Elution: The elution was continued with at least 10 column volumes of PBS at an appropriate flow rate (0.5 mL/min). The protein at the target UV peak was collected.

6.2.4. Endotoxin Removal and Detection a) Endotoxin Removal i. Sample processing: The ion strength was adjusted to 0.2±0.5 M with 1 M sodium chloride before purification, and the pH was adjusted to 7.4±0.2 with 0.1 M sodium hydroxide or 0.1 M hydrochloric acid.

ii. Resin activation: PD-10 column was fixed vertically, and the cap on the top of the pre-packed column was removed. The ToxinEraser™ Endotoxin Removal resin was loaded onto the column. The flow controller was turned on, allowing the protectant to drain by gravity. 5 ml of regeneration buffer was added, and the flow rate was kept at 0.25 mL/min (about 10 drops/min) by adjusting the flow controller. Additional 5 ml of regeneration buffer was added again when the regeneration buffer was drained. The procedure was repeated twice in order to ensure that the system remained pyrogen-free (i.e., endotoxin-free);

iii. Resin equilibration: When the activation of PD-10 columns was completed, 6 ml of equilibration buffer was added. The flow rate was kept at 0.5 ml/min by adjusting the flow controller, and then the equilibration buffer was drained. The procedure was repeated twice.

iv. Endotoxin removal: The flow controller was turned off. The sample was loaded by using pyrogen-free pipette tips. The controller was turned on to control the flow rate not higher than 0.25 mL/min. When the volume of the effluent reached 1.5 ml, the sample was loaded by using pyrogen-free tubes. Additional 1.5 ml-3.0 ml equilibration buffer was introduced for elution when the sample drained dry, and the eluate was collected. Sample concentration and the endotoxin level were determined (Bradford solution was used as an indicator of a complete collection during the Elution step).

b) Gel Clot Endotoxin Assay i. Sample dilution: Samples were diluted to an appropriate concentration (0.005 µg; 0.05 µg; 0.5 µg; 5 µg) depending on the requirement of TAL sensitivity (0.25 EU/ml);

ii. Dilution of endotoxin standard: Endotoxin standard was prepared, reconstituted in water for bacterial endotoxin detection, vortex mixed for 15 min, and then diluted to an appropriate concentration (0.5 EU/ml);

iii. Detection: TAL reagents were added into 100 µl water for bacterial endotoxin detection, and were gently shaken for at least 30 s until the reagents were completely dissolved. Air bubbles should be avoided. 100 µl of the following samples were added respectively: positive control (endotoxin standard 0.5 EU/ml), negative control (endotoxin free water) and diluted samples to be detected: samples to be detected at four different concentrations in (i). Tubes were sealed, gently shaken, placed vertically in a 37° C. incubator, incubated for 1 hour, and then removed for observation;

iv. Results recording: The test tubes were removed from the incubator gently, and put upside down 180° slowly. For the positive result, solid gel will be formed from the tube content, undistorted and will not slip off the tube wall; otherwise the result will be negative. The results of positive control tubes were positive, and the results of negative control tubes were negative, the status was the same in the same range, and thus the experiments were valid.

6.2.5. Filtration Sterilization

The Samples were filtrated with 0.22 µm filter aseptically in a biosafety cabinet, and an appropriate amount of the samples was set aside for subsequent assays.

6.2.6. Concentration and Purity Determination a) Determination of Protein Concentration i. According to the protein amino acid sequences provided, the absorbance coefficient of the protein was calculated.

ii. UV absorbance (A280) of the protein solution was detected.

iii. Protein concentration was calculated according to the formula: Protein concentration=UV absorbance (A280) of the protein solution/protein absorbance coefficient.

B) Protein Purity Determination

A certain amount of protein (e.g. 2 μg) according to the above determined concentration, and the same amount (e.g. 2 μg BSA) of the standard protein were subject to SDS-PAGE under reducing and non-reducing conditions. Thus the purity was tested and the concentration was determined.

EXAMPLE 7

HUVEC Cell Proliferation Inhibition Assay of the Single-domain Antibody 7.1. Cell Preparation About $3\times10^5$ HUVEC cells (ATCC, Cat No. PCS-100-010) were recovered and inoculated into a 10 cm culture dish, and the fresh medium was introduced into the culture dish every 3-4 days. Cells were split into different culture plates when they reached a 85%-95% confluence, and the fresh medium was added. Cells within the $7^{th}$ generation may be used for the cell proliferation inhibition assay, and typically cells of the $6^{th}$ generation will be used.

7.2. Inhibition Assay of HUVEC Proliferation Induced by VEGF

2×VEGF and different concentrations of antibody samples to be detected were prepared with a M199 buffer (Medium-199 1× Earle's Salts (Invitrogen #11150-059), 10% Fetal Bovine Serum (Gibco, Cat #10100139), heat inactivated; 10 mM HEPES (Invitrogen, Cat #15630080), 100 units/ml Penicillin 100 μg/ml Streptomycin (Invitrogen, Cat #10378016)) respectively. 50 μl 2×VEGF and different concentrations of antibody samples to be detected were premixed, respectively. Replicate microwells were set on the microwell plate. Treatment with the cell medium was used as the blank control, while treatment with Avastin was used as the positive control. The trypsinated cells were collected, washed with M199 buffer and resuspended twice to a final cell density of $1\times10^5$ cell/ml. 50 μL cell suspension solution was introduced into each well of the microwell plate. The cells added into the microwell plate were then placed in an incubator, and incubated at 37° C., 5% $CO_2$ for 96 hours. Cell viability was determined using CellTiter-Glo® Luminescent Cell Viability Assay Kit (Promega, Cat No: G7571) upon completion of the incubation. Meanwhile, the fluorescence intensity was determined by a PHERAStar Plus (BMG Labtech) reader, and the relative luminescence unit was recorded; The proliferation inhibition rate was calculated according to the following formula, Proliferation Inhibition Rate %=100*(1-Relative Luminescence Unit/Maximum production), wherein the relative luminescence unit was the determined value from each sample, and the Maximum production was the relative luminescence unit when only VEGF was added. By integrating both maximum inhibition and EC50 data, it was demonstrated that 6 out of 53 prokaryotic expressed single-domain antibodies showed significant inhibiting effect, which were selected for heavy-chain antibody construction and subsequent proliferation inhibition assay.

TABLE 7

EC50 values of HUVEC cell proliferation inhibition assay are as follows:

| Clone ID | EC50 (μg/ml) |
|---|---|
| A69451 | 0.5573 |
| A69452 | 0.4499 |
| A69457 | 0.4596 |
| A69458 | 0.1201 |
| A69462 | 0.0632 |
| A60724 | 0.0267 |
| A80723 | 0.1142 |
| A80744 | 0.1763 |
| A80730 | 0.2115 |
| A80890 | 0.6418 |
| A80726 | 0.1225 |
| A80887 | 0.0588 |
| A80740 | 0.7899 |

EXAMPLE 8

Expression of Heavy-chain Antibodies

The 6 single-domain antibodies with proliferation inhibiting effect from the initial screening in Example 7 and the 7 single-domain antibodies from receptor competitive screening were fused with the Fc fragment of human IgG1 (SEQ ID NO: 60) respectively to form a heavy-chain antibody construct, which was cloned into a pTT5 vector. The antibody was then expressed in HEK293E cells, and purified with removal of the endotoxin. Detailed procedures are as follows:

8.1. Reagents and Preparation

See Example 6.

8.2. Methods and Procedures 8.2.1. Cell Culture a) HEK293 suspension cells were removed from the liquid nitrogen or −86° C. refrigerator, immediately put in a 37° C. water bath, and thawed within 1~2 min.

b) The thawed cells were added into 10 times volume of preheated FreeStyle™ 293 Expression Medium, mixed upside down gently, collected by low-speed centrifuge and resuspended in an appropriate amount of freshly preheated medium.

d) The resuspended cells were transferred into a flask and incubated at 37° C., 5% $CO_2$, 110 rpm.

8.2.2. Transfection a) One day before transfection, HEK293 suspension cells were subcultured at a proper density to achieve $1.5-2.0\times10^6$ cells/ml on the day of transfection, and the cell viability was required to be higher than 95%.

b) An appropriate amount of DNA was thoroughly mixed with PEI at an optimal ratio (such as 1:3) in the preheated FreeStyle™ 293 Expression Medium, and the mixture was allowed to stand for 10 minutes at room temperature.

C) The aforementioned PEI-DNA mixture was added into cell culture, spun and mixed gently. The incubation continued at 37° C., 5% $CO_2$, 110 rpm.

D) Within 16-24 hours post transfection, Tryptone N1 at a final concentration of 0.5% (w/v) was added.

E) On the $6^{th}$ day post transfection, the culture supernatant was collected by centrifugation and filtrated with a 0.22 μm filter for subsequent purification.

8.2.3. Protein Purification

A) Affinity Purification by Protein A i. Equilibration: 5 column volumes of $ddH_2O$ and Binding Buffer were used for the equilibration of the Protein A packings.

ii. Binding: The filtrated supernatant was mixed with column packings and then incubated for binding for 1 h. Upon completion of the incubation, the column packings were loaded onto a PD-10 manual purification column.

iii. Washing: The column was washed with at least 30 column volumes of Binding Buffer to remove protein impurity (Bradford solution was used as an indicator during the Washing step: 5 µl washing solution was added into 200 µl Bradford staining solution. If the color turned blue, then the washing of protein impurities continued until the color of the staining solution remained essentially unchanged. Then proceeded to the next step).

iv. Elution: The target protein was eluted using at least 10 column volumes of Elution Buffer, and the pH was adjusted to approximately 7.0 with Neutralization Buffer (Bradford solution was used as an indicator of a complete elution during the Elution step, and the procedure was the same as step iii).

b) Desalination/Buffer Exchange:

The protein from affinity purification was exchanged to PBS buffer using HiTrap™ Desalting column on ä KTA Purifier 10 system. The subsequent steps of endotoxin removal, filtration sterilization, and concentration & purity determination were the same as those described in Example 6.

TABLE 8

Correspondence between Cone ID of the single-domain antibody and heavy chain antibody, as well as the sequence identifier for amino acid and nucleotide sequence of the variable region

| Clone ID of single-domain antibody | Clone ID of heavy chain antibody | amino acid sequence identifier | nucleotide sequence identifier |
|---|---|---|---|
| A14575 | A69451 | SEQ ID NO: 37 | SEQ ID NO: 50 |
| A14942 | A69452 | SEQ ID NO: 38 | SEQ ID NO: 51 |
| A15411 | A69457 | SEQ ID NO: 39 | SEQ ID NO: 52 |
| A14614 | A69458 | SEQ ID NO: 36 | SEQ ID NO: 49 |
| A14972 | A69462 | SEQ ID NO: 40 | SEQ ID NO: 53 |
| A10981 | A60724 | SEQ ID NO: 41 | SEQ ID NO: 54 |
| A15578 | A80723 | SEQ ID NO: 35 | SEQ ID NO: 48 |
| A15922 | A80744 | SEQ ID NO: 42 | SEQ ID NO: 55 |
| A15637 | A80730 | SEQ ID NO: 43 | SEQ ID NO: 56 |
| A15908 | A80890 | SEQ ID NO: 44 | SEQ ID NO: 57 |
| A15612 | A80726 | SEQ ID NO: 45 | SEQ ID NO: 58 |
| A15775 | A80887 | SEQ ID NO: 34 | SEQ ID NO: 47 |
| A15872 | A80740 | SEQ ID NO: 46 | SEQ ID NO: 59 |

EXAMPLE 9

HUVEC Cell Proliferation Inhibition Assay of the Heavy-chain Antibody 13 heavy-chain antibodies (Table 8) were 1:4 gradient diluted to eight concentrations starting from 20 µg/ml, and the procedure was the same as described in Example 7 except that Avastin (A68467) was used as the control. From the inhibition level on the cell proliferation by different concentrations of the antibody, it can be judged that 13 heavy-chain antibodies all showed inhibiting effect at varying degrees (FIG. 11), among which A80887, A80723 and A69458 showed the greatest inhibition at the cellular level. In particular, for A69458, it showed significantly superior inhibiting effect compared with the control, when the antibody concentration was $10^{-3}$~1 µg/ml; For A80723, it showed significantly superior inhibiting effect compared with the control, when the antibody concentration was $10^{-3}$~$10^{-1}$ µg/ml; For A80887, it showed significantly superior inhibiting effect compared with the control, when the antibody concentration was $10^{-2}$~1 µg/ml.

TABLE 9

Sample of the heavy chain antibody

| Clone ID | Endotoxin level (EU/µg) | Concentration (mg/ml) | Remarks |
|---|---|---|---|
| A69451 | <1 | 0.49 | |
| A69452 | <1 | 0.23 | |
| A69457 | <1 | 0.29 | |
| A69458 | <5 | 0.29 | |
| A69462 | <1 | 1.06 | |
| A60724 | <1 | 0.58 | |
| A80723 | <1 | 0.51 | |
| A80744 | <1 | 0.33 | |
| A80730 | <1 | 0.48 | |
| A80890 | <1 | 0.20 | |
| A80726 | <1 | 0.31 | |
| A80887 | <1 | 0.29 | |
| A80740 | <1 | 0.49 | |

EXAMPLE 10

Evaluation of the Anti-Angiogenesis Effect by the Antibody According to the Present Invention Using Zebrafish Model Samples to be detected (A80887), with a molecular weight of approximately 75 kDa, and a concentration of 5.1 mg/ml, were stored in aliquots at −80° C., diluted with 1×PBS (pH 7.4) immediately prior to use, and were kept on ice during the injection. The equipments and reagents used include: microinjector (IM300, Narishige), dissecting microscope (SMZ645, Nikon Corporation); electric focusing zoom fluorescence microscope (AZ100. Nikon); 6-well plate (Nest Biotech); MESAB (Sigma), and Bevacizumab (brand name Avastin, Roche).

Embryos of transgenic zebrafish with vascular fluorescence were obtained from breeding by natural mating 4~5 pairs of adult zebrafish were prepared for each mating, and thus an average of 200~300 embryos can be obtained from each pair. Embryos were cleaned (dead embryo was removed) 6 hours after fertilization (i.e. 6 hpf) and at 24 hpf, and proper embryos were selected according to their development stages (Kimmel, 1995). Embryos were incubated with fish culture water at 28° C. (Quality of fish culture water: 200 mg instant sea salt was added into each 1 L reverse osmosis water, conductivity was 480~510 µS/cm; pH was 6.9~7.2: water hardness was 53.7~71.6 mg/L $CaCO_3$). There is no need for embryos to be fed within 9 days after fertilization (9 dpf), since the embryos could obtain nutrients from their own yolk sac. Upon the completion of the procedure, the zebrafish at various developmental stages was anesthetized by exposing to excessive tricaine methane sulfonate. All procedures were performed in strict line with the international laboratory animal assessment and accreditation (AAALAC) standard.

By using the microinjector, the sample was injected at the highest concentration and the maximum injection volume into the blood circulation of the transgenic zebrafish with fluorescence in the blood vessels (equivalent to an intravenous administration for human), and no death or obvious abnormal phenotypes were found. Based on the above experimental results, 3 doses including 1/10 maximum injection dose (maximum concentration×maximum injection volume), 1/3 maximum injection dose, and the maximum injection dose were selected for detection, while a positive control group (Avastin), a solvent control group (PBS) and a blank control group were defined, 30 fish were treated in each group. A certain period of time post administration, 15 zebra fish were randomly selected from each group and photographed under a fluorescent microscope, and then the quantitative analysis of the subintestinal vessels (SIVs) area was performed. Statistical analysis was performed with a T-test between two groups, and with a one-way ANOVA and Dunnett's T-test among more groups, in which p<0.05 indicates a statistically significant difference. The angiogenesis inhibiting efficiency can be calculated according to the following formula:

$$\text{Angiogenesis inhibition rate} = \left(1 - \frac{S \text{ (drug treatment group)}}{S \text{ (solvent group)}}\right) \times 100\%$$

There were no deaths or abnormal phenotypes in all experimental groups during the whole procedure. There was no statistically difference between the blank control group and solvent control group (p>0.05); while there was a statistically difference between the positive control group (Avastin) and solvent control group (p<0.05).

During the preliminary experimentation for a proper dose, no deaths or obvious abnormal phenotypes were found using the greatest concentration of 5.1 mg/ml for injection. Therefore, 40.8 ng (0.544 pmol), 136 ng (1.81 pmol), and 408 ng (5.44 pmol) are chosen as the total doses for administration.

The experimental results demonstrated that, the angiogenesis inhibition rate was 10.9% (p>0.05), 18.5% (p<0.05) and 23.2% (p<0.001) respectively when A80887 dose was 20.4 ng (0.272 pmol), 68 ng (0.907 pmol) and 204 ng (2.72 pmol). The angiogenesis inhibition rate was 6.9% (p>0.05) and 19.5% (p<0.01) respectively when the Avastin dose was 400 ng (2.68 pmol) and 1 µg (6.7 pmol), and p<0.05 between these two doses. At the same molar mass (both were about 2.7 pmol), the angiogenesis inhibiting efficiency of A80887 was 23.2%, which was obviously better than 6.9% of Avastin (p<0.001). However, no statistical difference was observed for angiogenesis inhibiting efficiency between Avastin 1 µg (6.7 pmol) and A80887 20.4 ng (0.272 pmol), 68 ng (0.907 pmol) and 204 ng (2.72 pmol). The original data were shown in the following table.

The zebrafish angiogenesis model for pharmacodynamic assessment and new drug-target validation is widely accepted. Currently, several anticancer drugs which have entered into the pre-clinical trial stage or clinical trial stage (including FDA approved drugs), such as Vatalanib (Novartis) (Chan, 2002), Thalidomide (Celgene) (Yabu, 2005), Compound 6 (TargeGen) (Murphy, 2010), Rosuvastatin (Wang 2010), Solenopsin (Eli Lilly) (Arbiser, 2007), etc., have been successfully verified using the zebrafish angiogenesis inhibition model. Typically, the subintestinal vessels (SIVs) or the intermetameric vessels of a transgenic zebrafish with vascular fluorescence were selected for the evaluation of angiogenesis effect by a compound, and thus in this study, the quantitative analysis of the subintestinal vessels (SIVs) area was used for the evaluation of angiogenesis effect by sample A80887.

Avastin is a recombinant human monoclonal IgG1 antibody which binds to vascular endothelial growth factor (VEGF) and prevents its binding with the surface receptor (Flt-1 and KDR) of the endothelial cell. Avastin (molecular weight of 149 kDa) was selected in this study as the positive control of macromolecular drug for inhibiting angiogenesis. The experimental results demonstrated that Avastin showed good angiogenesis inhibiting effect and, therefore, it is reliable to use Avastin as the positive control for the evaluation.

In summary, ① Both A80887 and Avastin showed significant inhibiting effect on angiogenesis of the zebrafish. ② Compared with Avastin, A80887 showed obviously superior inhibiting effect on angiogenesis at the same molar mass (about 2.7 pmol). ③ When A80887 dose was 20.4 ng, 40.8 ng, 68 ng, 136 ng, 204 ng and 408 ng respectively, the corresponding reference dose for human administration was about 81.6, 163.2, 272, 544, 816 and 1632 µg/kg body weight.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

TABLE 10

Inhibition of A80887 on angiogenesis

| No. | Control | PBS | Avastin 1 µg | Avastin 400 ng | A80887 20.4 ng | A80887 68 ng | A80887 204 ng |
|---|---|---|---|---|---|---|---|
| 1 | 28570 | 25256 | 17558 | 21458 | 29976 | 21313 | 23713 |
| 2 | 32065 | 29797 | 24571 | 32339 | 27791 | 27964 | 18080 |
| 3 | 37021 | 23013 | 25549 | 27167 | 23297 | 17394 | 17747 |
| 4 | 28673 | 25430 | 21128 | 24991 | 20170 | 18220 | 23999 |
| 5 | 28975 | 28480 | 13377 | 24967 | 25530 | 20615 | 23189 |
| 6 | 28339 | 26380 | 25086 | 23503 | 23249 | 29979 | 21405 |
| 7 | 28935 | 31562 | 14578 | 23961 | 22736 | 22681 | 16435 |
| 8 | 23813 | 25505 | 22460 | 27848 | 21046 | 16633 | 19774 |
| 9 | 29959 | 26899 | 22546 | 22500 | 22210 | 25864 | 17904 |
| 10 | 37825 | 26429 | 24451 | 23191 | 27868 | 22022 | 18429 |
| 11 | 37873 | 23567 | 21695 | 29455 | 21018 | 22680 | 22039 |
| 12 | 37653 | 23676 | 22753 | 26385 | 23571 | 15169 | 21179 |
| 13 | 26171 | 24986 | 20942 | 20935 | 27618 | 23078 | 20235 |
| 14 | 21934 | 30155 | 24472 | 28212 | 26562 | 21085 | 19751 |
| 15 | 20596 | 33174 | 24169 | 19367 | 17349 | 24991 | 26435 |
| mean | 29893 | 26954 | 21689 | 25085 | 24011 | 21979 | 20688 |
| SD | 5672 | 3049 | 3745 | 3508 | 3479 | 4135 | 2807 |
| CV | 19 | 11 | 17 | 14 | 14 | 19 | 14 |
| SE | 1464 | 787 | 967 | 906 | 898 | 1068 | 725 |

The invention claimed is:

1. An anti-VEGF antibody or fragment thereof, wherein the antibody or fragment thereof comprises a heavy chain variable region, wherein the heavy chain variable region comprises:
   CDR1, CDR2 and CDR3 as set forth in SEQ ID NO: 1, SEQ ID NO: 2 and SEQ ID NO: 3 respectively.

2. The anti-VEGF antibody or fragment thereof according to claim 1, wherein the heavy chain further comprises a constant region.

3. The anti-VEGF antibody or fragment thereof according to claim 1, wherein the heavy chain further comprises an Fc region.

4. The anti-VEGF antibody or fragment thereof according to claim 1, wherein the antibody or fragment thereof is a camelid antibody consisting of heavy chains.

5. The anti-VEGF antibody or fragment thereof according to claim 1, wherein the antibody or fragment thereof is a monoclonal antibody, a chimeric antibody or a humanized antibody or fragment thereof.

6. The anti-VEOF antibody or fragment thereof according to claim 1, wherein the antibody or fragment thereof is a single-domain antibody.

7. The anti-VEGF antibody or fragment thereof according to claim 1, wherein the sequence of the heavy chain variable region of the antibody or fragment thereof is set forth in SEQ ID NO; 34.

8. A pharmaceutical composition comprising the anti-VEGF antibody or fragment thereof according to claim 1, and a pharmaceutically acceptable excipient.

9. The pharmaceutical composition according to claim 8, further comprising one or more therapeutically active compounds.

10. An antibody drug conjugate, comprising the anti-VEGF antibody or fragment thereof according to claim 1 conjugated to another agent.

11. An antibody drug conjugate according, to claim 10, wherein the conjugate further comprises a linker.

12. A kit comprising
   a) the anti-VEGF antibody or fragment thereof according to claim 1; and
   b) instructions for using the kit.

13. A method for inhibiting VEGF activity, comprising administering an effective amount of the anti-VEGF antibody or fragment thereof according to claim 1.

14. A method for inhibiting angiogenesis, comprising administering to a patient in need thereof an effective amount of the antibody or fragment thereof according to claim 1.

15. A method for treating a VEGF related disease or disorder, comprising administering to a patient in need thereof an effective amount of the antibody or fragment thereof according to claim 1, wherein the disease or disorder is a tumor or cancer or eye disease.

16. The method according to claim 15, wherein the tumor or cancer is breast cancer, brain tumor, renal carcinoma, ovarian carcinoma, thyroid carcinoma, lung cancer, colorectal cancer, endometrial cancer, angiosarcoma, bladder cancer, cancer of embryonic tissue, cervical tumor, malignant glioma, gastric cancer, pancreatic cancer or nasopharyngeal carcinoma.

17. The method according to claim 15, wherein the eye disease is macular edema, age-related macular degeneration, diabetic retinopathy, central retinal vein occlusion, neovascular glaucoma and other eye diseases involving neovascularization.

18. The method according to claim 17, wherein the macular edema is diabetic macular edema, macular edema after cataract operation, or macular edema caused by uveitis.

* * * * *

UNITED STATES PATENT AND TRADEMARK OFFICE
CERTIFICATE OF CORRECTION

PATENT NO. : 10,456,466 B2  
APPLICATION NO. : 15/101472  
DATED : October 29, 2019  
INVENTOR(S) : Fang et al.

Page 1 of 1

It is certified that error appears in the above-identified patent and that said Letters Patent is hereby corrected as shown below:

On the Title Page

Item (56) References Cited, OTHER PUBLICATIONS, Page 2, Column 2, Line 1, Li et al. cite: Please correct "Neovascualr" to read -- Neovascular --

In the Specification

Column 11, Line 66: Please correct "Vandien" to read -- Vandlen --

Column 25, Line 29, Table 8: Please correct "Cone ID" to read -- Clone ID --

In the Claims

Column 63, Line 45, Claim 7: Please correct "ID NO; 34" to read -- ID NO: 34 --

Signed and Sealed this  
Tenth Day of March, 2020

Andrei Iancu  
*Director of the United States Patent and Trademark Office*